(12) United States Patent
Liang et al.

(10) Patent No.: US 11,576,973 B2
(45) Date of Patent: *Feb. 14, 2023

(54) PHARMACEUTICAL FORMULATIONS THAT FORM GEL IN SITU

(71) Applicant: IVIEW Therapeutics, Inc., Cranbury, NJ (US)

(72) Inventors: Bo Liang, Plainsboro, NJ (US); Gang Wei, Shanghai (CN); John J. Baldwin, Gwynedd Valley, PA (US)

(73) Assignee: IVIEW Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/307,989

(22) PCT Filed: Oct. 25, 2016

(86) PCT No.: PCT/US2016/058722
§ 371 (c)(1),
(2) Date: Oct. 31, 2016

(87) PCT Pub. No.: WO2017/074965
PCT Pub. Date: May 4, 2017

(65) Prior Publication Data
US 2017/0266294 A1 Sep. 21, 2017

Related U.S. Application Data

(60) Provisional application No. 62/246,073, filed on Oct. 25, 2015.

(51) Int. Cl.
| | | |
|---|---|---|
| *A61K 47/36* | (2006.01) | |
| *A61K 47/32* | (2006.01) | |
| *A61K 33/18* | (2006.01) | |
| *A61K 47/10* | (2017.01) | |
| *A61K 9/00* | (2006.01) | |
| *A61K 47/26* | (2006.01) | |
| *A61K 9/06* | (2006.01) | |
| *A61K 31/155* | (2006.01) | |
| *A61K 31/79* | (2006.01) | |
| *A61K 47/02* | (2006.01) | |

(52) U.S. Cl.
CPC ............ *A61K 47/36* (2013.01); *A61K 9/0014* (2013.01); *A61K 9/0048* (2013.01); *A61K 9/06* (2013.01); *A61K 31/155* (2013.01); *A61K 31/79* (2013.01); *A61K 33/18* (2013.01); *A61K 47/02* (2013.01); *A61K 47/10* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 5,252,318 A | 10/1993 | Joshi et al. | |
| 6,261,547 B1 * | 7/2001 | Bawa | A61K 9/0048 424/78.04 |
| 6,281,192 B1 | 8/2001 | Leahy et al. | |
| 7,767,217 B2 | 8/2010 | Samson et al. | |
| 2003/0232089 A1 | 12/2003 | Singh et al. | |
| 2007/0098677 A1 | 5/2007 | Asgharian | |
| 2007/0167526 A1* | 7/2007 | Zhang | A61K 9/0019 514/649 |
| 2008/0086195 A1* | 4/2008 | Atanasoka | C23C 26/00 623/1.15 |
| 2011/0082221 A1 | 4/2011 | Haug et al. | |
| 2014/0322345 A1 | 10/2014 | Liang et al. | |

FOREIGN PATENT DOCUMENTS

| | | | |
|---|---|---|---|
| CN | 1377706 A | | 11/2002 |
| EP | 19860402170 | * | 10/1986 |
| WO | 0119366 A1 | | 3/2001 |

OTHER PUBLICATIONS

Paulsson et al. (Rheological Studies on the Gelation of Deacetylated Gellan Gum (Gelrite®) in Physiological Conditions). European Journal of Pharmaceutical Sciences. vol. 9, Issue 1, Oct. 1999.*
Kumar et al. (Designing of a Temperature Induced Povidone Iodide in situ Gel for Ophthalmia Neonatrorum) Journal of Pharmacy Research 2012.*
Kouchak et al. In situ gelling systems for drug delivery. (Year: 2014).*
McDonald, Marguerite B. et al. Efficacy and Safety of Besifloxacin Ophthalmic Suspension 0.6% Compared with Moxifloxacin Ophthalmic Solution 0.5% for Treating Bacterial Conjunctivitis. Amer Acad of Op, 2009; 116:1615-1623.
Mundada, A.S. et al. Formulation and Evaluation of Ciprofloxacin Hydrochloride Soluble Ocular Drug Insert. Curr Eye Res, 2008; 33:469-75.
Sieg, James W. et al. Vehicle Effects on Ocular Drug Bioavailability I: Evaluation of Fluorometholone. J Pharm Sci, 1975; 64:931-6.
Ganguly, Sudipta et al. A novel in situ gel for sustained drug delivery and targeting. Int J Pharm, 2004; 276:83-92.
Miller, Susan C. et al. Effect of poloxamer 407 gel on the miotic activity of pilocarpine nitrate in rabbits. Int J Pharm, 1982; 12:147-52.

(Continued)

*Primary Examiner* — David J Blanchard
*Assistant Examiner* — Sarah J Chickos
(74) *Attorney, Agent, or Firm* — Weisun Rao; Sunyong Tang; Venture Partner, LLC

(57) ABSTRACT

The present invention provides aqueous formulations containing an anti-infection agent, a biocompatible polysaccharide, an osmotic pressure regulator, a pH regulator, and water, wherein a gel containing the therapeutic agent is formed in situ upon instillation of the formulations onto the skin and a body cavity of a subject. The formulations of this invention are useful for treating infectious diseases of skin or a body cavity (e.g., eye, nose, or vagina) of a subject.

17 Claims, 8 Drawing Sheets

(56) References Cited

OTHER PUBLICATIONS

Gurny, Robert et al. Ocular therapy with nanoparticulate systems for controlled drug delivery. J Contr Rel, 1985; 2:353-61.
Rozier, A. et al. Gelrite®: A novel, ion-activated, in-situ gelling polymer for ophthalmic vehicles. Effect on bioavailability of timolol. Int J Pharm, 1989; 57:163-8.
Lin, Hong-Ru et al. Carbopoi/pluronic phase change solutions for ophthalmic drug delivery. J Contr Rel, 2000;69:379-88.
Hui, Ho-Wah et al. Ocular delivery of progesterone using a bioadhesive polymer. Int J Pharm, 1985; 26:203-13.
Sanzgiri, Yeshwant D. et al. Gellan-based systems for ophthalmic sustained delivery of methylprednisolone. J Contr Rel, 1993; 26:195-201.
Meseguer, G. et al. Gamma scintigraphic study of precorneal drainage and assessment of miotic response in rabbits of various ophthalmic formulations containing pilocarpine. Int J Pharm, 1993; 95:229-34.
Carlfors, Johan et al. Rheological evaluation of Gelrite® in situ gels for ophthalmic use. Eur J Pharm Sci, 1998; 6:113-9.
Cao, Yanxia et al. Poly(N-isopropylacrylamide)-chitosan as thermosensitive in situ gel-forming system for ocular drug delivery. J Contr Rel, 2007; 120:186-94.
Miyazaki, S. et al. In situ gelling xyloglucan formulations for sustained release ocular delivery of pilocarpine hydrochloride, Int J Pharm, 2001; 229:29-36.
Liu, Yuejiang et al. In Situ Gelling Gelrite/Alginate Formulations as Vehicles for Ophthalmic Drug Delivery. AAPS PharmSciTech, vol. 11, No. 2, Jun. 2010, 610-620.
Agnihotri, Sunil A. et al. Controlled release of cephalexin through gellan gum beads: Effect of formulation parameters on entrapment efficiency, size, and drug release, Eur J Pharm Biopharm, 2006; 63:249-61.
Balasubramaniam, Jagdish et al. In vitro and in vivo evaluation of the Gelrite® gellan gum-based ocular delivery system for indomethacin. Acta Pharm, 2003; 53:251-61.
Balakrishnan, Biji et al. Evaluation of an in situ forming hydrogel wound dressing based on oxidized alginate and gelatin. Biomaterials, 2005; 26:6335-42.
Liu, Zhidong et al. Study of an alginate/ HPMC-based in situ gelling ophthalmic delivery system for gatifloxacin. Int J Pharm, 2006; 315:12-17.
Lin, Hong-Ru et al. In Situ Gelling of Alginate/Pluronic Solutions for Ophthalmic Delivery of Pilocarpine. Biomacromolecuies, 2004; 5:2358-65.
Pongjanyakul, Thaned et al. Xanthan-alginate composite gel beads: Molecular interaction and in vitro characterization. Int J Pharm, 2007; 331:61-71.
Wu, Chunjie et al. Preparation and Evaluation of a Carbopol®/HPMC-based In Situ Gelling Ophthalmic System for Puerarin. Yakugaku Zasshi, 2007; 127:183-91.

* cited by examiner

PHARMACEUTICAL FORMULATIONS THAT FORM GEL IN SITU

CROSS-REFERENCE TO RELATED APPLICATIONS

This application is a U.S. national phase application of international application No. PCT/US2016/058722, filed on Oct. 25, 2016, which claims priority to U.S. Application No. 62/246,073, filed on Oct. 25, 2015, the contents of which are incorporated herein in their entirety.

BACKGROUND OF THE INVENTION

Infectious conjunctivitis is an ophthalmic disorder characterized by inflammation of the conjunctiva secondary to invasion of a microbe. Microbes capable of causing conjunctivitis in humans include bacteria (including Mycobacteria sp), viruses, fungi, and amoebae. Current treatments for bacterial conjunctivitis consist of antibiotic drops. Because antibiotic drops are ineffective against viral conjunctivitis, treatments for such infections can only relieve symptoms. Treatments for fungi and amoeba conjunctivitis consist of a small selection of medications which lack sufficient antibacterial or anti-viral activity and are sometimes toxic to the ocular surface.

Diagnosis of the various causative agents, such as bacteria, virus, or fungus, in infectious conjunctivitis is not economically feasible because accurate diagnosis requires sophisticated laboratory culture not easily integrated into the average healthcare practice. Because accurate diagnosis is impractical, most conjunctivitis is presumed to be bacterial without culturing and is treated with antibiotics. Antibiotic treatment is suboptimal because it is ineffective against viral or fungal conjunctivitis. In summary, there is currently no ophthalmic antimicrobial drug that has broad activity against all the causes of conjunctivitis or keratitis and can be safely used in infectious conjunctivitis or keratitis that can potentially be viral or fungal in origin.

Ophthalmic topical drug delivery is one of the important methods of application, but the existence of cornea barrier, tear dilution and lacrimal passage drainage effect limit the treatments and bioavailability of many topical ophthalmic preparations. The conventional liquid ocular formulation is eliminated from the precorneal area immediately upon instillation because of lachrymation and effective nasolacrimal drainage. See, e.g., VHL Lee et al., J. Pharm. Sci., 1979; 68: 673-84. Various preparations, such as ointments, suspensions, inserts, and hydrogels, have been developed for ophthalmic delivery system not only to slow down the drug elimination but also to lengthen the residence time of the vehicle on ocular surface. See W. I. Higuchi, J. Pharm. Sci., 1962; 51: 802-4; M. B. McDonald et al., Optometry, 2009; 80: 296-7; A. S. Mundada et al., Curr. Eye Res., 2008; 33: 469-75; and J. W. Sieg et al., J. Pharm. Sci., 1975; 64: 931-6. However, they have not been used extensively because of some drawbacks, such as blurred vision with ointments or low patient compliance with inserts. See, e.g., B. K. Nanjawade et al., J. Contr. Rel., 2007; 122: 119-34.

An ideal ophthalmic formulation should be administrated in eye drop form, without causing blurred vision or irritation. This problem can be overcome using in situ gel-forming drug delivery systems prepared from polymers that exhibit sol-to-gel phase transitions due to a change in a specific physicochemical parameter in the cul-de-sac. See, e.g., S. Ganguly et al., Int. J. Pharm., 2004; 276: 83-92.

In the past few years, an impressive number of pH- (e.g., cellulose acetate phthalate and Carbopol), temperature- (e.g., Poloxamer), and ion- (e.g., gellan gum and alginate) induced in situ forming systems have been reported to sustain ophthalmic drug delivery. See, e.g., S. C. Miller et al., Int. J. Pharm., 1982; 12: 147-52; R. Gurny et al., J. Contr. Rel., 1985; 2:353-61; A. Rozier et al., Int. J. Pharm., 1989; 57:163-8; and H. R. Lin et al., J. Contr. Rel., 2000; 69: 379-388. These in situ gel-forming systems could prolong the precorneal residence time of a drug and improve ocular bioavailability. See, e.g., H. W. Hui et al., Int. J. Pharm., 1985; 26: 203-213; Y. D. Sanzgiri et al., J. Contr, Rel. 1993; 26:195-201; G. Meseguer et al., Int. J. Pharm., 1993; 95: 229-234; J. Carlfors et al., Eur. J. Pharm. Sci., 1998; 6: 113-119; Y. X. Cao et al., J. Contr. Rel., 2007; 120:186-194; S. Miyazaki et al., Int. J. Pharm., 2001; 229: 29-36; Y. Liu et al., AAPS PharmSciTech, 11 (2), June 2010, 610-620; CN Patent No. ZL 02109503.5 (2007) to G. Wei et al.

The choice of a special hydrogel depends on its intrinsic properties and envisaged therapeutic use, Deacetylated gellan gum (DGG, an exocellular polysaccharide of microbial origin, commercially available as Gelrite®) is an interesting in situ gelling polymer that has been tested since it seems to perform very well in humans. See, A. Rozier et al., Supra; Y. Liu et al., Supra; and S. A. Agnihotri et al., Eur. J. Pharm. Biopharm., 2006; 63: 249-261. Preparations of Gelrite are dropped into eyes; gel formation takes place, induced by the electrolytes of the tear fluid. See, e.g., J. Balasubramaniam et al., Acta Pharm., 2003; 53: 251-261. The other in situ gelling compound examined, sodium alginate, is widely used in pharmaceutical preparation. See, e.g., B. J. Balakrishnana et al., Biomaterials, 2005; 26: 6335-6342; and Z. Liu et al., Int. J. Pharm., 2006; 315: 12-17.

Similarly, aqueous solutions of alginate (a natural polysaccharide extracted from brown sea algae) also form gels when instilled into the eye. It was previously reported that Joshi et al. used a combination of polymers in the delivery system to reduce total polymer content and improve gelling properties. See, e.g., U.S. Pat. No. 5,252,318, to Joshi et al. They demonstrated that aqueous compositions reversibly gelled in response to simultaneous variations in at least two physical parameters (e.g., pH, temperature, and ionic strength) can be formed by using a combination of polymers that exhibit reversible gelation properties. Many authors, on the basis of this finding, have developed the similar delivery system to improve patient compliance and therapeutic activity. See, e.g., H. R. Lin et al., Biomacromolecules, 2004; 5: 2358-2365; T. Pongjanyakul et al., Int. J. Pharm., 2007; 331: 61-71; and C. J. Wu et al., Yakugaku Zasshi, 2007; 127: 183-191.

Povidone iodine (PVP-I) is a complex of polyvinylpyrrolidone and iodine. It is also called iodophor and contains 9-12% effective iodine. It is a powerful disinfectant with a broad spectrum of applications and is strongly effective against viruses, bacteria, fungi, and mold spores. It causes little irritation on skin and has low toxicity and lasting effect, and can be used safely and easily. It basically does not cause irritation on tissue and is widely used for skin and mucous membrane disinfection, e.g., for pre-surgical cleaning and disinfection of surgical site and wound. The principle of sterilization is mainly through the release of hydrated iodine which has bactericidal effect. Povidone is hydrophilic and can carry iodine to cell membrane. When the complex arrives at the cell wall, the iodine is released and then complexes with amino acids of bacterial protein to denature it and, at the same time, oxidize the active groups of the bacteria's protoplasmic protein so that the bacteria dies rapidly. PVP-I is a very good bactericidal agent with no antibiotic resistance. In common use, povidone iodine's concentration is between 0.1% and 10%. Current PVP-I preparations are in the forms of gel, suppository, cream, and solution, with concentration ranging from 1% to 10%. See Chinese Pharmacopoeia 2010 Edition. PVP-I eye drops have been widely used for the treatment of ocular infection basically with high concentrations of 5% with toxic effects that cannot be ignored. Grimes and others treated infected eyes repeatedly with 0.02% PVP-I eye drops which have the same germicidal effects as one with concentration of 5.0% PVP-I but without the toxic affection and irritation. See, e.g., S. R. Grimes et al., Mil. Med., 1992, 157:111-113. In order to retain the PVP-I eye drops' sterilizing effect, but also eliminate its toxicity to eyes, clinical operation usually use PVP-I eye drops with concentration of 0.04% to disinfect eyes with no noticeable toxicity. We have previously reported a low concentration PVP-I in combination with dexamethasone eye drops as potential treatment for acute conjunctivitis, and currently the drug candidate has finished phase II clinical trials. See, e.g., U.S. Pat. No. 7,767,217 B2. However, at a low concentration, PVP-I will degrade quickly, and its concentration cannot be effectively maintained during storage or at the infected site due to the tear barrier effects. Therefore, in order to reduce the toxic effect on the eyes by PVP-I at a high concentration while maintaining its pharmaceutical effect at the infected site, it is often necessary to prepare formulations with low toxicity and long-lasting effect.

However, as a result of strong oxidizing potential and acidity of water-soluble PVP-I polymer material, it is difficult to prepare PVP-I extended release formulation from common slow release technologies such as ointments, microsphere, or hydrogels. We have developed a PVP-I alginate microsphere technology (see, US Patent Application Publication No. 2014/0322345 or WO 2013/078998 A1) and successfully developed a PVP-I alginate microsphere cured by $CaCl_2$; however, it was also observed that an in-situ gel formulation of alginate and PVP-I cannot be achieved. We suspect such non-gel formation was due to acidity of PVP-I resulting on low gel strength of alginate in-situ gel. Therefore there is a need to develop stable hydrogel PVP-I formulations which have good gel strength, slow-releasing properties, and non-irritation to the eye.

Developing long-acting and good compliance ophthalmic preparations has always been an important challenge for the current ophthalmic rational drug use. The in situ gel delivery system is a novel dosage form that utilizes the property of the polymer to be sensitive to environmental factors and is administered in the form of a solution, forming a gel in local. This combines both the advantages of the solution and the gel and avoids both disadvantages and shows an ideal application prospect.

The mechanism of in situ gel formation is to utilize polymer materials' features of changing dispersion or conformation under different environmental conditions, resulting in a significant increase of solution viscosity, thus forming a gel-state drug reservoir in drug administration sites. Correspondingly, the in situ gel can be categorized into three main types: temperature-sensitive, ion-sensitive and pH-sensitive in situ gels.

Deacetylated gellan gum (DGG), an anionic deacetylated extracellular polysaccharide secreted by *Pseudomonas Elodea*, is tetra-saccharide repeating units formed by polymerization of one molecule of α-L-rhamnose, one molecule of β-D-glucuronic, and two molecules of β-D-glucoses. Deacetylated gellan gum has temperature-dependent and cation-induced gelation properties, and a certain concentration of deacetylated gellan gum solution can form a moderate viscosity and strong water-holding gel with the cations in the tears. (Ophthalmological composition of the type which undergoes liquid-gel phase transition. See, e.g., U.S. Pat. No. 4,861,760 to C. Mazuel et al.) Merck's Timoptic-XE®, a long-acting ophthalmic timolol maleate formulation, has been shown to improve ocular bioavailability and reduce the frequency of drug administration. Comparing non-gelled polymer solutions with Timoptic-XE®, it was discovered that the gelation mechanism is an important factor for improved efficacy. Rheological studies showed that the 0.5% to 1% Gelrite® aqueous solution only need 10%-25% of the ions in the tears to transform into a gel, in which $Na^+$ plays the most important role to promote the gel formation. In vitro release assay showed that indomethacin in situ gel ophthalmic solution can sustain release drug for 8 hours. Comparing with the traditional ophthalmic preparation, the ion-sensitive in situ gel has the obvious advantages, such as long residence time in cornea, thus improved bioavailability; good histocompatibility and dosing accuracy; ability to stay in flowing liquid state before use, thus easy to fill, and easy for industrial production.

Gellan gum concentrations of 0.5% to 1% (w/w) are required for in situ gel formation in all marketed products containing gellan gum. Moreover, since gellan gum is ion-sensitive, the inorganic salt such as sodium chloride cannot be added as osmotic pressure regulator in its formulation.

The present invention provides an in situ gel-formation ophthalmic formulation containing povidone iodine ("PVP-I"). PVP-I is a polymer drug with significantly different physical and chemical properties, such as strong acidity, water-solubility, ion complex equilibrium, comparing to all reported small molecule drugs, which potentially affect gellan gum's gel-forming ability. However, we have surprisingly discovered that povidone iodine's addition into polysaccharide natural polymer materials such as deacetylated gellan gum, reduces the required gellan gum concentration in order for gel-formation significantly. Gellan gum's concentration can be less than 0.5% (w/w) in compositions containing PVP-I when mixing with the simulated tear to form a gel. Although gellan gum has an ion-sensitive property, its viscosity does not increase at physiological temperature (34° C.) due to the dilution of simulated tear after mixing with simulated tear. Therefore gellan gum itself cannot form in-situ gel in the eye upon instillation. However, we surprisingly found that the viscosity of the gellan gum solution containing PVP-I is significantly increased at physiological temperature (34° C.) which shows a typical in-situ gel property after mixing with simulated tear.

Moreover, we surprisingly discovered that adding an appropriate concentration of sodium chloride as osmotic pressure regulator into compositions containing povidone-iodine and gellan gum will cause a significant thixotropy of the formulation. The composition will transform into a semi-solid gel state after sitting still for a few hours, but it can quickly turn into a free-flowing fluid with a gentle shake of the container. In addition, the addition of appropriate concentration of sodium chloride in PVP-I and gellan gum compositions makes the composition more sensitive to tear ions to form gel when mixing with tears. The composition not only extends PVP-I's retention time in the conjunctival sac with slower dissolution and extended release of the drug, but also can reduce povidone iodine's irritation to the eye. The stability of such extended release in situ gel PVP-I composition is improved over its corresponding solution formulation, making it more suitable for clinical applications.

SUMMARY OF THE INVENTION

This present invention provides aqueous formulations each comprising an anti-infection agent, a biocompatible polysaccharide, an osmotic pressure regulator, a pH regulator, and water, wherein a gel containing the therapeutic agent is formed in situ upon instillation of the formulation onto the skin and a body cavity of a subject. Examples of infectious disease in the eye (ocular infectious disease) include, but are not limited to, conjunctivitis, corneal abrasion, ulcerative infectious keratitis, epithelial keratitis, stromal keratitis, or herpes virus-related keratitis; examples of infection disease in the nose include chronic rhinosinusitis and acute rhinosinusitis; and an example of vaginal infection is vaginitis. Other pharmaceutically acceptable excipients or therapeutic agents (e.g., anti-inflammatory agents) may also be included in the aqueous formulations of this invention. When the formulations are used for treating ocular infectious diseases, they can be called ophthalmic formulations.

In some embodiments, the anti-infection agent contained in the aqueous formulations of this invention includes povidone-iodine (PVP-I) or chlorhexidine.

In some other embodiments, the therapeutic agent is contained in the aqueous ophthalmic formulation at 0.1% to 5.0% (weight/weight or weight/volume, e.g., at 0.1% to 1.0% (weight/weight or weight/volume), at 0.1% to 0.6% (weight/weight or weight/volume) or at 0.3% to 0.6% (weight/weight or weight/volume).

In some other embodiments, the biocompatible polysaccharide is contained in the aqueous formation at 0.1% to 0.5% (weight/weight), e.g., at 0.3% to 0.4% (weight/weight).

In some other embodiments, the biocompatible polysaccharide contained in the aqueous formulation includes deacetylated gellan gum (DGG), xanthan, sodium alginate, carrageenan, or any mixture thereof.

In some other embodiments, the osmotic pressure regulator contained in aqueous ophthalmic formulation includes sodium chloride, glycerol, polyethylene glycol 400 (PEG400), mannitol, or boric acid.

In some other embodiments, the osmotic pressure regulator is contained in the formulation at 0.1 to 0.5% (w/v), e.g., at 0.2 to 0.4% (w/v).

In some other embodiments, the pH regulator contained in the aqueous ophthalmic formulation includes sodium hydroxide, tris(hydroxymethyl)aminomethane (Tris), phosphoric acid, or any mixture thereof.

In some other embodiments, the aqueous formulations have a pH value in the range of 5.0 to 9.0, or in the range of 5.0 to 6.0.

Unexpectedly, the aqueous formulations of this invention provide a more extended (i.e., longer) release of the therapeutic agent when compared to a non-gel-forming formulation.

Also within the scope of this invention is a method for treating or preventing an infectious disease, which includes administering a therapeutically effective amount of an aqueous formulation of this invention to skin and a body cavity of a subject of a subject in need thereof. The cavity of a subject can be eye, nose, or vagina. Examples of the infectious disease in the eye include conjunctivitis, corneal abrasion, ulcerative infectious keratitis, epithelial keratitis, stromal keratitis, and herpes virus-related keratitis; examples of the infection disease in the nose include chronic rhinosinusitis and acute rhinosinusitis; and an example of the vaginal infection is vaginitis.

In general, the aqueous formulations of this invention have an obvious thixotropy. They may form semi-solid gels under normal standing-still conditions, but can change into free-flowing liquids immediately when shaken before use. When used for treating an ocular infectious disease, after dripping into the conjunctival sac, an aqueous ophthalmic formulation of this invention can spread on the ocular surface to form in situ a gel and prolong the residence time of the therapeutic agent (e.g., PVP-I) on the ocular surface, thereby becoming a more effective administration of the therapeutic agent and requiring less frequent administration. Additionally, the aqueous ophthalmic formulations of this invention have the advantages of reducing ocular irritation that may be caused by the therapeutic agent (e.g., PVP-I). The aqueous ophthalmic formulations of this invention are useful in the treatment of active infections of the conjunctiva and cornea induced by, for example, bacterial, mycobacterial, viral, fungal, or amoebic causes, as well as treatment to prevent such infections in appropriate clinical settings (e.g. corneal abrasion, postoperative prophylaxis, post-LASIK/LASEK prophylaxis, or radial keratotome).

As used herein, the term "subject" means a mammal and includes human and non-human.

As used herein, the term "gel" refers to a solid jelly-like material that can have properties ranging from soft and weak to hard and tough and exhibits no flow when in the steady-state.

In addition, anti-inflammatory can be added into the aqueous formulations of this invention for clinical benefits. Moreover, the aqueous formulations of this invention may be made more effective by the addition of a dilute topical anesthetic, e.g., for elimination of pain associated with the drop and enhanced penetration of anti-infective compounds into ocular structures. Accordingly, the aqueous formulations of this invention are also effective in the prevention of infection and/or inflammation in the post-operative patients.

As used herein, the term "anti-infection agent" refers to a therapeutic agent that has the effect to eliminate or reduce the infectious symptoms.

As used herein, the term "polysaccharide" refers to a polymeric carbohydrate molecule composed of long chains of monosaccharide units bound together by glycosidic linkages and on hydrolysis give the constituent monosaccharides or oligosaccharides. They can be natural or synthetic, and they range in structure from linear to highly branched. Examples include storage polysaccharides such as starch and glycogen, and structural polysaccharides such as cellulose and chitin.

As used herein, the term "biocompatible" refers to the ability of a material to perform with an appropriate host response in a specific situation.

As used herein, the word "a" or "an" can be interpreted to introduce a plural form of a noun, unless such interpretation results in contrary or inoperative meaning.

As used herein, the work "or" shall also mean "and" unless such interpretation results in contrary or inoperative meaning.

BRIEF DESCRIPTIONS OF THE FIGURES

DETAILED DESCRIPTION OF THE INVENTION

Figure 1:
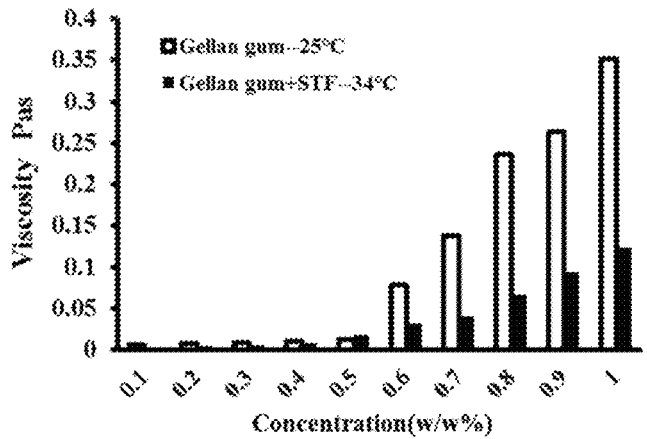
FIG. 1 shows the viscosity change of a DGG solution at the room temperature (25° C.) and under simulated physiological conditions (mixing with STF by ratio 40:7, 34° C.).

The aqueous formulations in this invention contain a therapeutic agent against an infectious disease of skin or cavity of a subject (i.e., a mammal), a biocompatible (and environmentally sensitive) polysaccharide, an osmotic pressure regulator, a pH regulator, water, and optionally other pharmaceutically acceptable excipient or vehicles. The cavity can be eye, nose, or vagina.

The ocular infection disease may be conjunctivitis, corneal abrasion, ulcerative infectious keratitis, epithelial keratitis, stromal keratitis, or herpes virus-related keratitis; whereas the infection disease in the nose can be chronic rhinosinusitis or acute rhinosinusitis; and the vaginal infection can be vaginitis. The polysaccharide contained in the formulations of this invention may include deacetylated gellan gum (DGG), xanthan, sodium alginate and carrageenan, or a mixture of these materials. Deacetylated gellan gum may be preferred, with a concentration ranging from 0.1% to 1% (w/w)—e.g., from 0.3% to 0.5% (w/w)—in the formulations.

The therapeutic agent contained in the formulations may be PVP-I or chlorhexidine. The concentration of the PVP-I may range from 0.1% to 5% (w/w or w/v), from 0.3% to 1% (w/w or w/v), or from 0.3% to 0.6% (w/w or w/v). An example of chlorhexidine suitable for the formulations of this invention is chlorhexidine digluconate, with its concentration in the formulations ranging from 0.02% to 2% (w/w or w/v), from 0.02% to 0.5% (w/w or w/v), or from 0.02% to 0.2% (w/w or w/v).

The osmotic pressure regulator contained in the formulations of this invention may include sodium chloride, glycerol, polyethylene glycol 400 (PEG400), mannitol, or borate, with a concentration ranging from 0.1 to 0.9% (w/v) or from 0.2 to 0.4% (w/v).

The pH regulator contained in the formulations of this invention can include sodium hydroxide, trishydroxymethylaminomethane (Tris), or phosphoric acid, resulting in a pH of 5 to 9 or 5.0 to 6.0.

The invention is further elucidated with specific examples. It is understood that these examples are only used to describe the invention but not to intend to limit the scope of invention. The experimental methods with no specific conditions in the following examples, are usually prepared under conventional conditions in the literature or according to the conditions suggested by the excipient manufacturer. Unless specifically stated, all percentages, ratios, proportions or fractions in this invention are calculated by weight by weight. Unless specifically defined in this invention, all professional and scientific terms used herein have the same meaning as well-trained personnel may be familiar with. In addition, any methods and materials similar or equivalent to those recorded in this invention can be applied to this invention. The preferred embodiments and materials described herein are used only for exemplary purposes.

Example 1

Preparation of solution of deacetylated gellan gum (DGG) (Kelcogel-Cg-La gellan gum, food grade gellan gum, CAS: 71010-52-1: E418, particle size: ~42 mesh (355 μm), purchased from CPKelco): DGG was dissolved in deionized water and the solution was stirred in an 80° C. water bath for 1 hour, cooled to the room temperature, allowed to stand until the material is fully swollen, and used to prepared solutions of 0.1% to 1.0% (w/w) concentrations.

Preparation of simulated tear fluid (STF): $NaHCO_3$ 2.18 g; NaCl 6.78 g; $CaCl_2 \cdot 2H_2O$ 0.084 g; KCl 1.38 g; dissolve in 1000 mL deionized water: DGG solution and simulated tear fluid were mixed at the 40:7 ratio, and the viscosity of the DGG solution was measured before and after mixing with stimulated tear fluid with a rotary rheometer at 25° C. and at 34° C., respectively. The viscosity change was shown in FIG. 1. For the DGG solution in a concentration range of 0.1% to 1.0% (w/w), its viscosity was reduced significantly under simulated physiological condition (mixing with STF by ratio 40:7, 34° C.) comparing with DGG solution alone at the room temperature (25° C.), which suggested that DGG alone could not form in situ gel under physiological conditions and that it would be necessary to further add a gel modifier into DGG solution to give it a better gel-forming ability. Sodium alginate, kappa-carrageenan, and xanthan were added into the DGG solution in a certain proportion, respectively, and the rheological properties of resultant mixed solutions were evaluated to screen an appropriate gel modifier.

Example 2

DGG-Xanthan mixed solution: DGG and xanthan were weighed and used at a certain proportion and added into deionized water. The mixture was stirred in an 80° C. water bath for 1 hour after the dispersion of DGG and xanthan in the water, cooled to the room temperature, and allowed to stand until fully swollen. The morphological scoring of the deacetylated gellan gum-xanthan mixed solution before and after adding simulated tear fluid was evaluated according to the following criteria: (1) thin liquid: 1-3 points; (2) thick gelatinous form: 4-6 points; (3) gel state: 7-9 points.

TABLE 1

Morphological scoring of the DGG-xanthan solutions before and after adding STF.

| DGG (%, w/w) | Xanthan (%, w/w) | Scoring D + X 25° C. | Scoring D + X + STF (25° C.) | Scoring D + X + STF 34° C. Δ |
|---|---|---|---|---|
| 0.3 | 0.1 | 1 | 2 | 1 |
| | 0.2 | 1 | 3 | 2 |
| | 0.3 | 2 | 3 | 1 |
| | 0.4 | 3 | 5 | 2 |
| | 0.5 | 3 | 6 | 3 |
| | 0.6 | 3 | 7 | 4 |
| 0.4 | 0.1 | 2 | 3 | 1 |
| | 0.2 | 2 | 3 | 1 |
| | 0.3 | 2 | 4 | 2 |
| | 0.4 | 5 | 6 | 1 |
| 0.5 | 0.1 | 2 | 3 | 1 |
| | 0.2 | 2 | 4 | 2 |
| | 0.3 | 3 | 4 | 1 |
| 0.6 | 0 | 2 | 4 | 2 |
| | 0.1 | 3 | 3 | 0 |
| | 0.2 | 4 | 4 | 0 |
| | 0.3 | 5 | 5 | 0 |
| | 0.4 | 5 | 5 | 0 |

Figure 2:
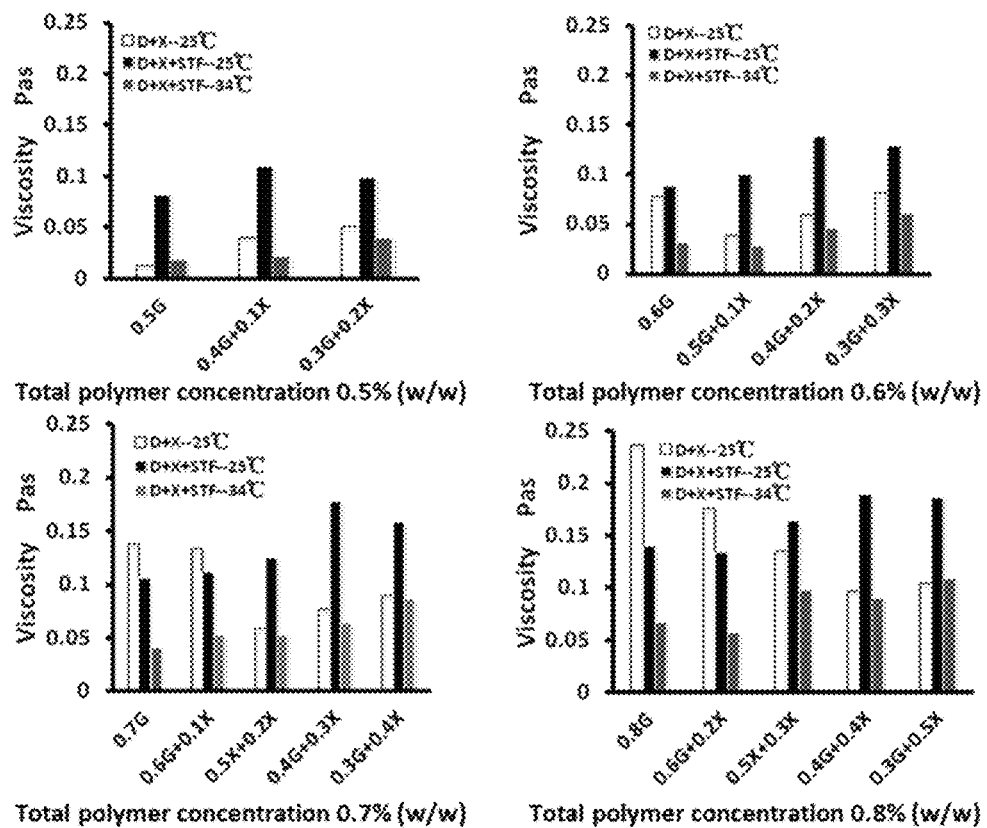
FIG. 2 shows the viscosity change of a DGG-xanthan solution at the room temperature (25° C.) and under simulated physiological conditions (mixing with STF by ratio 40:7, 34° C.).

As shown in Table 1 and FIG. 2, the viscosity change tendency of DGG-xanthan solution was consistent with the change of DGG solution alone under both room temperature 25° C. and simulated physiological conditions at 34° C. Specifically, the viscosity increased after adding simulated tear fluid but decreased with increasing temperature, so it is still not an ideal in situ gel system.

Example 3

DGG-Kappa-Carrageenan compound solution: DGG and carrageenan were weighed and used at a certain proportion, added into deionized water, and the mixture was slowly stirring in an 80° C. water bath for 1 hour after being well-dispersed. It was then cooled to the room temperature and allowed to stand until fully swollen. The morphological scoring of the DGG-kappa-carrageenan mixed solutions before and after adding tear fluid was evaluated according to the above-mentioned criteria.

TABLE 2

The morphological scoring of the DGG-kappa-carrageenan mixed solution before and after adding STF.

| DGG (%, w/w) | Kappa-Carrageenan (%, w/w) | D + K | 25° C.- D + K + STF | D + K + STF 34° C. Δ |
|---|---|---|---|---|
| 0.2 | 0.1 | 1 | 1 | 0 |
| | 0.2 | 1 | 1 | 0 |
| | 0.3 | 2 | 2 | 0 |
| | 0.4 | 2 | 5 | 3 |
| 0.3 | 0.1 | 1 | 1 | 0 |
| | 0.2 | 1 | 2 | 1 |
| | 0.3 | 2 | 7 | 5 |
| | 0.4 | 3 | 8 | 5 |
| 0.4 | 0.1 | 2 | 2 | 0 |
| | 0.2 | 2 | 6 | 4 |
| | 0.3 | 3 | 6 | 3 |
| 0.5 | 0.1 | 3 | 3 | 0 |
| 0.6 | 0.1 | 4 | 6 | 2 |
| | 0.2 | 4 | 6 | 2 |
| | 0.3 | 7 | 8 | 1 |
| | 0.4 | 8 | 9 | 1 |

Figure 3:
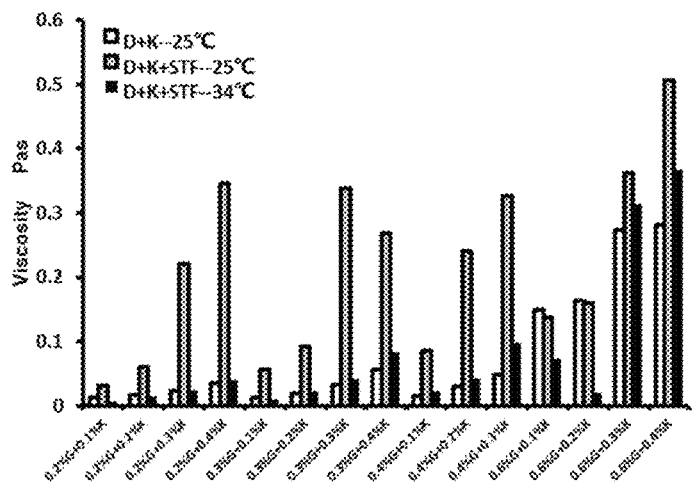
FIG. 3 shows the viscosity change of a DGG-carrageenan solution at the room temperature (25° C.) and under simulated physiological conditions (mixing with STF by ratio 40:7, 34° C.).

As the result shown in Table 2 and FIG. 3, the viscosity change tendency of DGG-carrageenan mixed was consistent with DGG solution alone at both the room temperature 25° C. and simulated physiological condition 34° C. The viscosity increased after adding simulated tear fluid but decreased with increasing temperature, so it is still not an ideal in situ gel system.

Example 4

DGG-Sodium alginate mixed solution: DGG and sodium alginate were weighed and used at a certain proportion. DGG was added into deionized water slowly under stirring in an 80° C. water bath for 1 hour after well-dispersed, cooled to room temperature, before sodium alginate was added to the solution by stirring. The mixture was allowed to stand for 24 hours until fully swollen. The morphological scoring of the resultant DGG-sodium alginate mixed solution before and after adding tear fluid was evaluated according to the above-mentioned criteria.

TABLE 3

Morphological scoring of the DGG-sodium alginate mixed solution before and after adding STF.

| DGG (%, w/w) | Alginate (%, w/w) | D + A | 25° C.- D + A + STF | D + A + STF 34° C. Δ |
|---|---|---|---|---|
| 0.2 | 0.1 | 1 | 1 | 0 |
| | 0.2 | 1 | 1 | 0 |
| | 0.3 | 1 | 1 | 0 |
| | 0.4 | 2 | 2 | 0 |
| | 0.5 | 2 | 2 | 0 |
| | 0.6 | 2 | 2 | 0 |
| | 0.8 | 2 | 2 | 0 |
| 0.3 | 0.1 | 1 | 1 | 0 |
| | 0.2 | 2 | 2 | 0 |
| | 0.3 | 2 | 2 | 0 |
| | 0.4 | 2 | 2 | 0 |
| | 0.5 | 2 | 2 | 0 |
| | 0.6 | 3 | 2 | 1 |
| | 0.8 | 4 | 2 | 2 |

TABLE 3-continued

Morphological scoring of the DGG-sodium alginate mixed solution before and after adding STF.

| DGG (%, w/w) | Alginate (%, w/w) | D + A | 25° C.-D + A + STF | D + A + STF 34° C. Δ |
|---|---|---|---|---|
| 0.4 | 0.1 | 1 | 1 | 0 |
|  | 0.2 | 2 | 2 | 0 |
|  | 0.3 | 2 | 2 | 0 |
|  | 0.4 | 3 | 3 | 0 |
|  | 0.6 | 4 | 3 | 1 |
|  | 0.8 | 5 | 3 | 2 |
| 0.5 | 0.2 | 3 | 3 | 0 |
|  | 0.4 | 4 | 3 | 1 |
|  | 0.6 | 5 | 3 | 2 |
|  | 0.8 | 6 | 4 | 2 |
| 0.6 | 0.1 | 4 | 3 | 1 |
|  | 0.2 | 5 | 3 | 2 |

Figure 4:
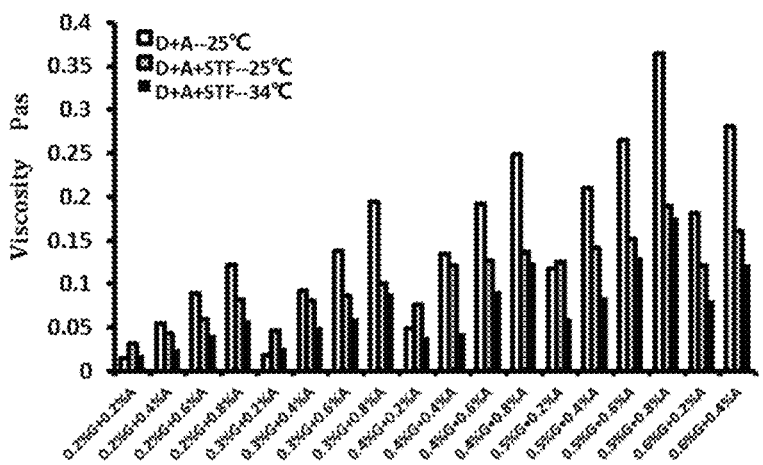
FIG. 4 shows the viscosity change of a DGG sodium alginate solution at the room temperature (25° C.) and under simulated physiological conditions (mixing with STF by ratio 40:7, 34° C.).

As the result shown in Table 3 and FIG. 4, after adding simulated tear fluid, the DGG-sodium alginate mixed solution's viscosity decreased at the room temperature 25° C., and further decreased when the temperature increased to 34° C. It was concluded that this system could not form in situ gel under physiological condition.

The above results indicated that addition of other macromolecule excipients to the DGG solution did not improve the gel-formation ability of DGG under simulated physiological conditions. PVP-I is a polymeric drug, and its effect on gel-formation ability when added to DGG solution was completely unknown.

Example 5

The effect of povidone iodine and osmotic pressure regulator mannitol on gel formation ability of deacetylated gellan gum solution was investigated. Prepare deacetylated gellan gum solutions, containing povidone iodine and osmotic pressure regulator mannitol, according to the formulation set out in Table 4 (referred as Formulation (G)). Evaluate physicochemical properties and viscosity of all formulations under room temperature (25° C.) and simulated physiological condition (Formulation: simulated tear fluid STF=40:7, 34° C.).

TABLE 4

The physicochemical properties of deacetylated gellan gum solutions, containing povidone iodine and mannitol.

|  | PVP-I (%, w/w) | D-mannitol (%, w/w) | Concentration of DGG (%, w/w) | pH | Osmotic pressure (mOsm/kg) |
|---|---|---|---|---|---|
| Formulation (G) | 0.6% | 5% | 0.30 | 5.31 | 292 |
|  |  |  | 0.35 | 5.08 | 301 |
|  |  |  | 0.40 | 5.22 | 291 |
|  |  |  | 0.45 | 5.15 | 287 |
|  |  |  | 0.5 | 5.18 | 279 |
|  |  |  | 0.55 | 5.11 | 300 |
|  |  |  | 0.6 | 5.69 | 303 |

Figure 5:
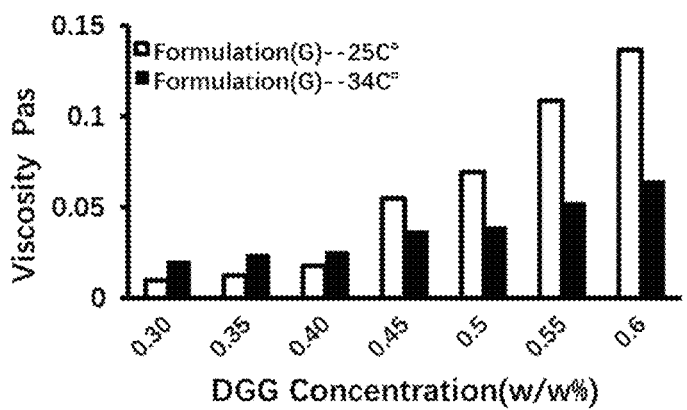
FIG. 5 shows the viscosity change of a DGG solution, containing povidone iodine and mannitol, at the room temperature (25° C.) and under simulated physiological conditions (mixing with STF by ratio 40:7, 34° C.).

As shown in Table 4 and FIG. 5, the addition of povidone iodine into deacetylated gellan gum solutions surprisingly and completely changed the gel-forming abilities of these solutions. After addition of povidone iodine, a few specific concentrations of deacetylated gellan gum solutions could form gel in situ (e.g., a formulation containing 0.45% (w/w) deacetylated gellan gum), and the gel would change into the liquid form after adjusting to the surrounding pH. For solutions/formulations containing 0.3%, 0.35%, 0.4% (w/w) deacetylated gellan gum, their viscosities under the simulated physiological conditions were greater than those under non-physiological conditions. These formulations in general exhibited in situ gelling ability under physiological conditions when DGG concentrations were optimized.

Example 6

The effect of povidone iodine and osmotic pressure regulator mannitol on gel-formation ability of xanthan solutions: Xanthan solutions, containing povidone iodine and osmotic pressure regulator mannitol, were prepared according to formulations set out in Table 5 (referred as Formulation (X)). The physicochemical properties and viscosity of all formulations were evaluated at the room temperature (25° C.) and under simulated physiological condition (formulation: simulated tear fluid STF=40:7, 34° C.).

TABLE 5

Physicochemical properties of xanthan solutions, containing PVP-I and mannitol.

|  | PVP-I (%, w/w) | D-mannitol (%, w/w) | Concentration of xanthan (%, w/w) | pH | Osmotic pressure (mOsm/kg) |
|---|---|---|---|---|---|
| Formulation (X) | 0.6% | 5% | 0.3 | 5.04 | 279 |
|  |  |  | 0.35 | 5.01 | 289 |
|  |  |  | 0.4 | 5.53 | 292 |
|  |  |  | 0.45 | 5.62 | 285 |
|  |  |  | 0.5 | 5.04 | 280 |

Figure 6:
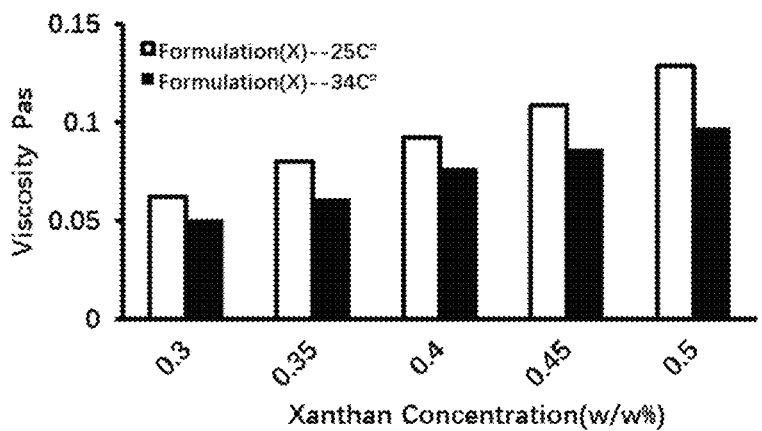
FIG. 6 shows the viscosity change of a xanthan solution, containing povidone iodine and mannitol, at the room temperature (25° C.) and under simulated physiological conditions (mixing with STF by ratio 40:7, 34° C.).

As shown in Table 5 and FIG. 6, for the formulations containing xanthan as gel-forming material, their viscosity increased after PVP-I was added to the formulations, but these formulations still could not form gel, and their viscosity under the simulated physiological conditions was slightly less than that under the non-physiological conditions.

Example 7

The effect of povidone iodine and osmotic pressure regulator mannitol on gel-formation ability of deacetylated gellan gum-carrageenan mixed solutions: prepare deacetylated gellan gum-carrageenan mixed solutions, containing povidone iodine and osmotic pressure regulator mannitol, according to the formulation set out in Table 6 (referred as Formulation (G+K)). Evaluate physicochemical properties and viscosity of all formulations under room temperature (25° C.) and simulated physiological condition (formulation: simulated tear fluid STF=40:7, 34° C.).

TABLE 6

Physicochemical properties of DGG-carrageenan mixed solutions, containing PVP-I and mannitol.

|  | PVP-I (%, w/w) | D-mannitol (%, w/w) | Total polymer (%, w/w) | Concentration (%, w/w) | pH | Osmotic pressure (mOsm/kg) |
|---|---|---|---|---|---|---|
| Formulation (G + K) | 0.6% | 5% | 0.2 | 0.1G + 0.1K | 5.6 | 298 |
|  |  |  | 0.3 | 0.1G + 0.2K | 5.24 | 299 |
|  |  |  |  | 0.2G + 0.1K | 5.41 | 293 |
|  |  |  | 0.4 | 0.1G + 0.3K | 5.21 | 308 |
|  |  |  |  | 0.2G + 0.2K | 5.86 | 296 |
|  |  |  |  | 0.3G + 0.1K | 5.24 | 287 |
|  |  |  | 0.5 | 0.1G + 0.4K | 5.11 | 311 |
|  |  |  |  | 0.2G + 0.3K | 5.05 | 300 |
|  |  |  |  | 0.3G + 0.2K | 5.38 | 296 |
|  |  |  |  | 0.4G + 0.1K | 5.17 | 294 |
|  |  |  | 0.6 | 0.1G + 0.5K | 5.26 | 290 |
|  |  |  |  | 0.2G + 0.4K | 5.15 | 300 |
|  |  |  |  | 0.3G + 0.3K | 5.25 | 295 |
|  |  |  |  | 0.4G + 0.2K | 5.06 | 292 |
|  |  |  |  | 0.5G + 0.1K | 5.34 | 296 |

Figure 7:
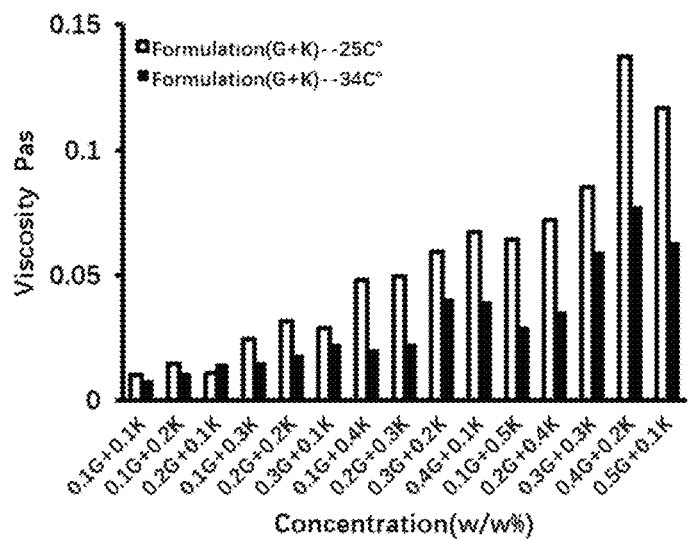
FIG. 7 shows the viscosity change of a DGG-carrageenan solution, containing povidone iodine and mannitol, at the room temperature (25° C.) and under simulated physiological conditions (mixing with STF by ratio 40:7, 34° C.).

As the result shown in Table 6 and FIG. 7, for formulations using deacetylated gellan gum-carrageenan as gel forming materials, their viscosity increased after adding povidone iodine, and some formulations formed gel upon mixing with STF. Except 0.2% G+0.1% K formulation, the rest of formulations' viscosity under simulated physiological condition was less than that under non-physiological condition.

Example 8

The effect of povidone iodine and osmotic pressure regulator mannitol on gel-formation ability of DGG-sodium alginate mixed solutions: A mixed solution of DGG and sodium alginate was prepared, containing PVP-I and an osmotic pressure regulator mannitol, according to the formulation set out in Table 6 (referred as Formulation (G+A)).

The physicochemical properties and viscosity of all formulations were evaluated at the room temperature (25° C.) and under simulated physiological conditions (prescription: simulated tear fluid STF=40:7, 34° C.).

TABLE 7

Physicochemical properties of DGG-sodium alginate mixed solution, containing povidone iodine and mannitol.

|  | PVP-I (%, w/w) | D-mannitol (%, w/w) | Concentration (%, w/w) | pH | Osmotic pressure (mOsm/kg) |
|---|---|---|---|---|---|
| Formulation (G + A) | 0.6% | 5% | 0.2G + 0.2A | 5.06 | 298 |
|  |  |  | 0.2G + 0.4A | 5.22 | 296 |
|  |  |  | 0.2G + 0.6A | 5.17 | 311 |
|  |  |  | 0.3G + 0.3A | 5.11 | 303 |
|  |  |  | 0.4G + 0.2A | 5.03 | 295 |

Figure 8:
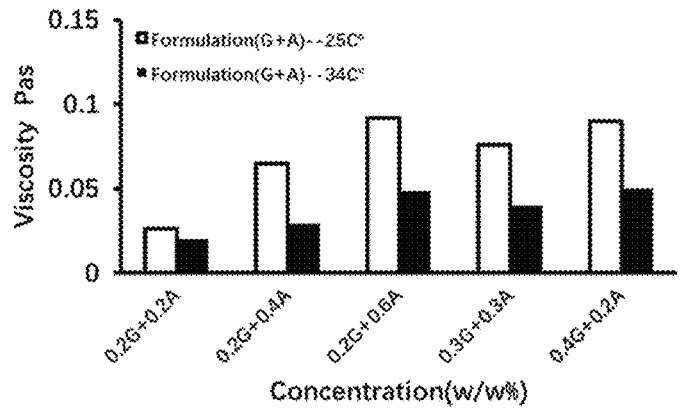
FIG. 8 shows the viscosity change of a DGG-sodium alginate solution, containing povidone iodine and mannitol, at the room temperature (25° C.) and under simulated physiological conditions (mixing with STF by ratio 40:7, 34° C.).

As the result shown in Table 7 and FIG. 8, for formulations containing DGG-sodium alginate as the gel forming materials, their viscosity increased after PVP-I was added, but could not form gel. Their viscosity under the simulated physiological condition was less than that under the non-physiological condition, thus they were not in situ gel forming systems (i.e., could not form gel).

Example 9

Simulation of viscosity change of formulations containing PVP-I caused by changes of temperature, shear stress, and tear flush after the formulations were dropped into conjunctival sac. Formulations of this invention containing PVP-I were prepared according to the formulations set out in Table 8. 5 mL of the formulations was taken and mixed with 1, 2, 3, 4, 5 parts of simulated tear fluid, respectively. 1 part simulated tear fluid equaled to 0.875 mL, and the calculation was based on the ratio of 40:7 between the formulations of this invention and simulated tear fluid. Viscosity of the formulations of this invention containing PVP-I and different concentrations of deacetylated gellan gum was measured, and diluted by different proportions of simulated tear fluid respectively.

TABLE 8

The formulations of povidone iodine in situ gel eye drops.

| Gellan gum Concentration (w/w %) | PVP-I (w/w %) | D-mannitol Concentration (w/w %) | Osmotic pressure (mOsm/kg) | pH |
|---|---|---|---|---|
| 0.3 | 0.6% | 5% | 294 | 6.2 |
| 0.35 |  |  | 298 | 6.52 |
| 0.4 |  |  | 291 | 6.47 |

5 ml of formulation of this invention containing PVP-I was taken. Added to the formulation was 0.875 mL simulated tear fluid and the mixture was well shaken before 1.5 mL sample was taken for viscosity determination. 0.875 mL simulated tear fluid was then added into the remaining solution, and another 1.5 mL of the resultant sample was taken out for viscosity determination. These steps were repeated 6 times, until the formulations were finished.

Figure 9:
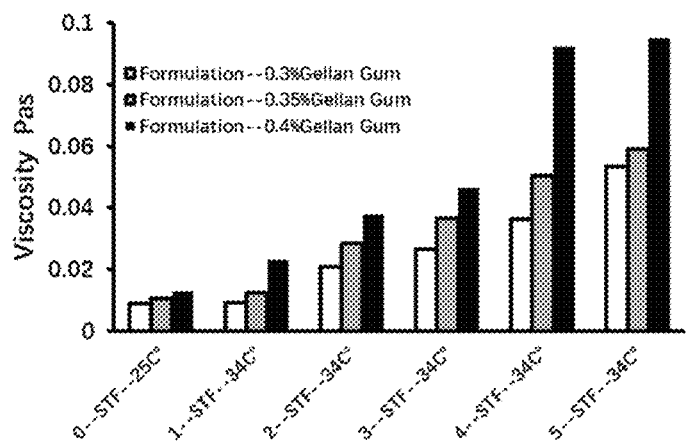
FIG. 9 shows the viscosity change of an ophthalmic formulation of this invention, containing PVP-I and different concentrations of DGG, after multiple dilution by simulated tear fluid.
Figure 10:
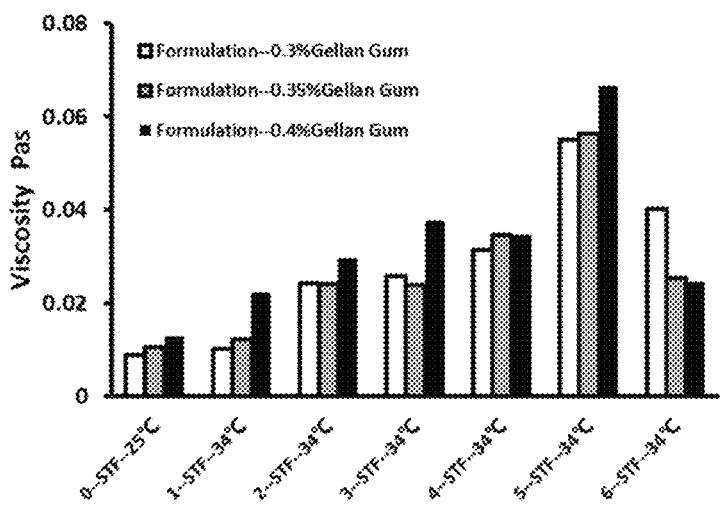
FIG. 10 shows the viscosity change of an ophthalmic formulation of this invention, containing PVP-I and different concentrations of DGG, after dilution and elimination by simulated tear fluid.

FIG. 9 shows the changes in viscosity of the simulated formulations of this invention in vivo containing PVP-I due to gradual dilution by tears in the eye. FIG. 10 shows the changes in viscosity of the simulated formulations of this invention containing PVP-I in vivo due to gradual dilution and elimination by tears in the eye. From FIG. 9 and FIG. 10 results, it can be seen that the viscosity of formulations of this invention containing PVP-I increased gradually with gradual dilution by the tears, indicating that it can form gel in conjunctival sac, and thus extending release of povidone iodine in the eye. After 6 times dilution by tears (STF), the viscosity of these formulations decreases, showing the gel formation ability starting to decline.

Example 10

Screening of osmotic pressure regulators: The effect of osmotic pressure regulator on the stability of povidone iodine solution under was evaluated at the room temperature (25° C.). 0.6 g povidone iodine was added into 100 mL deionized water, followed by adding an osmotic pressure regulator according to Table 9. The pH of the resultant mixture was adjusted to 5.0-5.5 with NaOH, and their stability was evaluated at 25° C. PVP-I concentration was determined by sodium thiosulfate titration (n=3).

TABLE 9

Formulations containing PVP-I, containing different osmotic pressure regulator

| Formulation | Osmotic pressure regulator | Amount (w/w) |
|---|---|---|
| 1 | Glycerol | 2.5% |
| 2 | PEG 400 | 5% |
| 3 | Mannitol | 5% |
| 4 | NaCl | 0.9% |
| 5 | Borate | 1.9% |

TABLE 10

Available iodine content (%) in PVP-I solutions. Assuming available iodine content at 0 day as 100% to calculate the remaining available iodine content after 5, 10 days.

| Example 10 | 0 day | | | | 5 day | | | Avg. | Remaining |
|---|---|---|---|---|---|---|---|---|---|
| | | | | Avg. | | | | | |
| PVP-I | 9.04 | 9.04 | 9.04 | 9.04 | 7.68 | 8.14 | 8.59 | 8.14 | 90.01% |
| PVP-I + Glyerol | 9.89 | 9.89 | 9.44 | 9.74 | 8.54 | 8.54 | 8.54 | 8.54 | 87.68% |
| PVP-I + PEG 400 | 10.38 | 10.38 | 10.38 | 10.38 | 8.13 | 8.58 | 8.58 | 8.43 | 81.21% |
| PVP-I + Mannitol | 9.54 | 9.54 | 9.54 | 9.54 | 8.63 | 8.63 | 8.63 | 8.63 | 90.46% |
| PVP-I + NaCl | 10.09 | 9.63 | 10.09 | 9.94 | 9.63 | 9.63 | 9.63 | 9.63 | 96.91% |
| PVP-I + Borate | 8.99 | 9.44 | 8.99 | 9.14 | 7.64 | 8.54 | 8.54 | 8.24 | 90.15% |

| Example 10 | 10 day | | | Avg. | Remaining |
|---|---|---|---|---|---|
| PVP-I | 4.23 | 4.65 | 4.65 | 4.51 | 49.89% |
| PVP-I + Glyerol | 5.56 | 5.56 | 5.56 | 5.56 | 57.08% |
| PVP-I + PEG 400 | 4.64 | 5.16 | 4.64 | 4.81 | 46.37% |
| PVP-I + Mannitol | 5.61 | 6.08 | 5.14 | 5.61 | 58.81% |
| PVP-I + NaCl | 6.14 | 6.14 | 6.14 | 6.14 | 61.79% |
| PVP-I + Borate | 5.55 | 5.09 | 5.55 | 5.40 | 59.04% |

Figure 11:
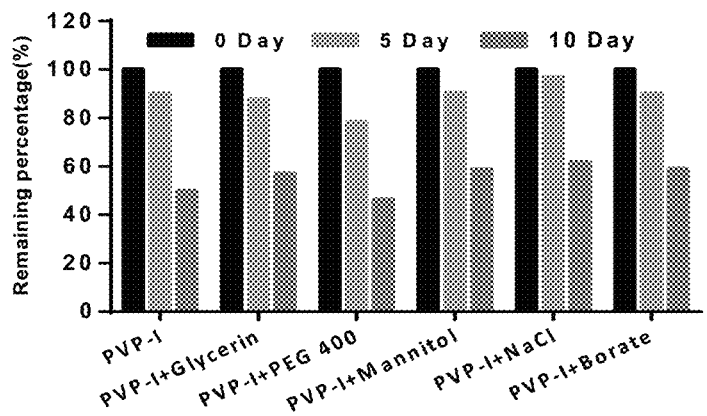
FIG. 11 shows the stability of a PVP-I solutions at 25° C., containing different osmotic pressure regulators.

As the result shown in Table 10 and FIG. 11, osmotic pressure regulators such as glycerol, mannitol, NaCl, and borate enhanced the stability of povidone iodine solution, and NaCl showed the best effect on PVP-I stability.

Screening of NaCl concentrations: NaCl was selected as osmotic pressure regulator. As DGG had an ionic sensitivity characteristic, we considered adding a small amount of NaCl in the formulation, so it did not form a gel while under storage condition, but gel formation would be triggered by mixing with a small amount of tear fluid in conjunctival sac. Formulations of this invention containing PVP-I and NaCl of different concentrations were prepared according to Table 10. Surprisingly, the formulations containing PVP-I and 0.3% NaCl showed a weak gel state after standing for a period of time. The formulations would become liquid of low viscosity immediately after shaking slightly, making them idea candidates for gelling.

TABLE 11

Gel-forming observation of the formulations of PVP-I in situ gel eye drops, containing different concentrations of NaCl

| Concentration of NaCl (%, w/w) | Characteristics |
|---|---|
| 0.1 | Liquid, no particles |
| 0.2 | Liquid, no particles |
| 0.3 | Weak gel state after 24 hours, become low viscosity liquid immediately after gentle shaking, no particles |
| 0.4 | Become hard gel after standing, partial broken gel particles after shaking |
| 0.5 | Become hard gel after standing, partial broken gel particles after repeatedly shaking |
| 0.6 | Become hard gel after standing, partial broken gel particles after repeatedly shaking |
| 0.7 | Become hard gel, partial broken gel particles after vigorously shaking |
| 0.8 | Become hard gel immediately, partial broken gel particles after vigorously shaking |
| 0.9 | Become hard gel immediately, hard to shake |

Example 11

Screening of pH regulators: The effect of pH regulator on the stability of povidone iodine solution was evaluated at the room temperature (25° C.). 0.9% normal saline (NS) was used as solvent, and 0.3% (w/w) DGG was used as gel matrix. NaOH, Tris, disodium hydrogen phosphate (DHP) and disodium hydrogen phosphate (DHP)-sodium dihydrogen phosphate+NaOH as pH regulator, was added respectively, to prepare PVP-I eye drops and formulations of this invention containing PVP-I at pH of 5.0-5.5. Their stability was evaluated at 25° C. Available iodine concentration was determined by sodium thiosulfate titration (n=3).

TABLE 12

PVP-I Formulations

| Formulation | NaCl (w/w) | Gellan gum (w/w) | pH regulator |
|---|---|---|---|
| NS | 0.9 | — | — |
| DGG | 0.3 | 0.3 | — |
| NS-NaOH | 0.9 | — | NaOH |
| DGG-NaOH | 0.3 | 0.3 | NaOH |
| NS-Tris | 0.9 | — | Tris |
| DGG-Tris | 0.3 | 0.3 | Tris |
| NS-Disodium hydrogen phosphate | 0.9 | — | Disodium hydrogen phosphate |
| DGG-Disodium hydrogen phosphate | 0.3 | 0.3 | Disodium hydrogen phosphate |
| NS-Phosphate buffer-NaOH | 0.9 | — | Phosphate buffer and NaOH |
| DGG-Phosphate buffer-NaOH | 0.3 | 0.3 | Phosphate buffer and NaOH |

TABLE 13

Available Iodine concentration (%) after 5, 10, 20, 30 days.

Available Iodine (%)

| Example 11 | 0 day | | | Avg. | 5 day | | | Avg. | Remaining |
|---|---|---|---|---|---|---|---|---|---|
| 0.9% Normal Saline (NS) | 11.61 | 11.61 | 11.61 | 11.61 | 11.47 | 11.06 | 11.06 | 11.20 | 96.44% |
| 0.3% DGG | 11.61 | 11.15 | 11.61 | 11.46 | 11.06 | 11.06 | 11.06 | 11.06 | 96.54% |
| NS-NaOH | 11.16 | 11.16 | 10.69 | 11.00 | 10.6 | 11.06 | 11.06 | 10.91 | 99.12% |
| DGG-NaOH | 11.17 | 11.17 | 11.17 | 11.17 | 10.62 | 10.62 | 10.62 | 10.62 | 95.08% |
| NS-Tris | 11.63 | 11.16 | 11.16 | 11.32 | 11.07 | 11.07 | 11.07 | 11.07 | 97.82% |
| DGG-Tris | 11.13 | 10.66 | 10.66 | 10.82 | 10.58 | 10.58 | 10.58 | 10.58 | 97.81% |
| NS-disodium hydrogen phosphate | 11.64 | 11.64 | 11.17 | 11.48 | 11.08 | 11.08 | 11.08 | 11.08 | 96.49% |
| DGG-disodium hydrogen phosphate | 11.63 | 11.63 | 11.17 | 11.48 | 11.08 | 11.08 | 11.08 | 11.08 | 96.54% |
| NS-phosphate buffer + NaOH | 11.65 | 11.19 | 11.19 | 11.34 | 11.1 | 10.63 | 10.63 | 10.79 | 95.09% |
| DGG-phosphate buffer + NaOH | 11.66 | 11.2 | 11.2 | 11.35 | 11.11 | 11.11 | 11.11 | 11.11 | 97.86% |

Available Iodine (%)

| Example 11 | 10 day | | | Avg. | Remaining |
|---|---|---|---|---|---|
| 0.9% Normal Saline (NS) | 11.09 | 11.09 | 11.09 | 11.09 | 95.52% |
| 0.3% DGG | 10.64 | 10.64 | 10.64 | 10.64 | 92.87% |
| NS-NaOH | 10.65 | 10.65 | 10.65 | 10.65 | 96.79% |
| DGG-NaOH | 10.22 | 10.22 | 10.67 | 10.37 | 92.84% |
| NS-Tris | 11.1 | 10.66 | 10.66 | 10.81 | 95.49% |
| DGG-Tris | 10.18 | 10.18 | 10.18 | 10.18 | 94.11% |
| NS-disodium hydrogen phosphate | 10.67 | 10.67 | 10.67 | 10.67 | 92.92% |
| DGG-disodium hydrogen phosphate | 10.66 | 10.66 | 10.22 | 10.51 | 91.61% |
| NS-phosphate buffer + NaOH | 10.68 | 10.68 | 10.68 | 10.68 | 94.15% |
| DGG-phosphate buffer + NaOH | 10.25 | 10.25 | 10.25 | 10.25 | 90.28% |

Available Iodine (%)

| Example 11 | 20 day | | | Average | Remaining | 30 day | | | Average | Remaining |
|---|---|---|---|---|---|---|---|---|---|---|
| 0.9% Normal Saline (NS) | 10.3 | 10.3 | 10.74 | 10.45 | 89.98% | 9.37 | 10.71 | 9.82 | 9.97 | 85.85% |
| 0.3% DGG | 9.85 | 9.85 | 9.85 | 9.85 | 85.98% | 9.37 | 9.37 | 10.26 | 9.67 | 84.38% |
| NS-NaOH | 9.41 | 9.85 | 9.85 | 9.70 | 88.19% | 9.38 | 9.38 | 9.82 | 9.53 | 86.58% |
| DGG-NaOH | 8.97 | 9.42 | 9.42 | 9.27 | 82.99% | 9.39 | 9.39 | 8.94 | 9.24 | 82.72% |
| NS-Tris | 9.86 | 9.86 | 8.97 | 9.56 | 84.51% | 9.38 | 9.38 | 9.38 | 9.38 | 82.89% |
| DGG-Tris | 9.83 | 8.94 | 9.38 | 9.38 | 86.75% | 8.91 | 8.91 | 8.91 | 8.91 | 82.37% |
| NS-disodium hydrogen phosphate | 9.87 | 9.87 | 9.87 | 9.87 | 85.95% | 9.84 | 9.84 | 8.94 | 9.54 | 83.08% |

TABLE 13-continued

| | Available Iodine concentration (%) after 5, 10, 20, 30 days. | | | | | | | | | |
|---|---|---|---|---|---|---|---|---|---|---|
| DGG-disodium hydrogen phosphate | 9.87 | 9.87 | 9.87 | 9.87 | 86.00% | 9.39 | 9.39 | 9.39 | 9.39 | 81.82% |
| NS-phosphate buffer + NaOH | 10.17 | 9.71 | 9.25 | 9.71 | 85.60% | 9.83 | 9.39 | 9.39 | 9.54 | 84.07% |
| DGG-phosphate buffer + NaOH | 9.89 | 8.99 | 8.99 | 9.29 | 81.83% | 9.41 | 9.41 | 9.41 | 9.41 | 82.88% |

Figure 12:
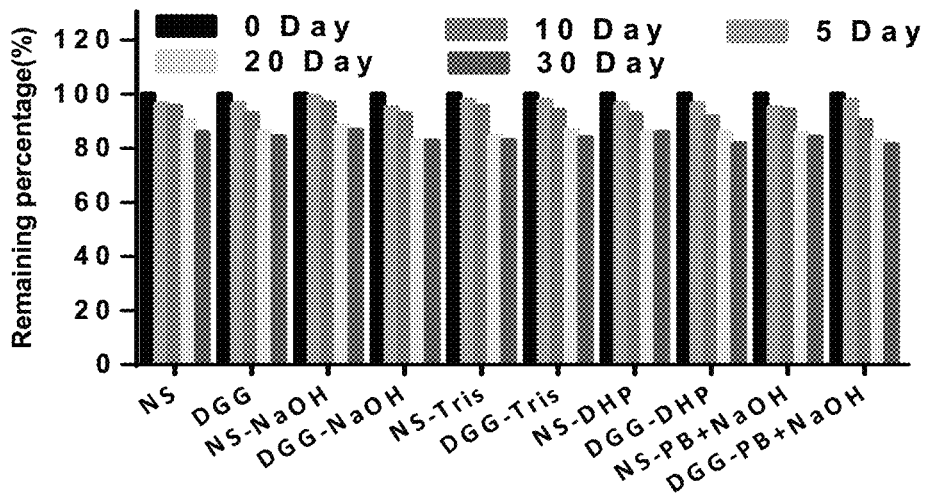
FIG. 12 shows the stability of a PVP-I solution and an ophthalmic formulation of this invention containing PVP-I at 25° C., containing different pH regulators.

As the result shown in able 13 and FIG. 12, after storage under 25° C. for 30 days, the stability of PVP-I solution and formulations of this invention containing PVP-I was slightly superior when NaOH was used as the pH regulator. Trishydroxymethylaminomethane (Tris) and hydrogen phosphates did not have a significant negative effect on PVP-I stability. The stability of formulations of this invention containing PVP-I was slightly better than that of PVP-I solution.

Example 12

Screening of pH range: The effect of pH range on the stability of PVP-I solution at the room temperature (25° C.) was evaluated. 0.9% normal saline (NS) was used as solvent, 0.3% (w/w) DGG was used as gel matrix, and NaOH was used to adjust the pH to 4-5, 5-6, 6-7, 7-8, 8-9, respectively, to give rise to formulations of this invention. The stability of these formulations was evaluate at 25° C., and the available iodine concentration was determined by sodium thiosulfate titration (n=3).

TABLE 14 pH changes of PVP-I solution and formulations of this invention containing PVP-I in different pH range

| | 0 Day | 5 Day | 10 Day | 20 Day | 30 Day |
|---|---|---|---|---|---|
| Solution-no pH adjust | 2.78 | 2.77 | 2.67 | 2.94 | 2.55 |
| In situ gel-no pH adjust | 3.28 | 3.3 | 3.19 | 3.45 | 3.08 |
| Solution-pH 4-5 | 4.47 | 4.3 | 4.1 | 4.23 | 3.56 |
| In situ gel-pH 4-5 | 4.47 | 4.53 | 4.11 | 4.33 | 3.81 |
| Solution-pH 5-6 | 5.38 | 4.53 | 4.32 | 4.45 | 4.06 |
| In situ gel-pH 5-6 | 5.21 | 4.65 | 4.39 | 4.5 | 4.19 |
| Solution-pH 6-7 | 6.42 | 4.84 | 4.58 | 4.65 | 4.01 |
| In situ gel-pH 6-7 | 6.56 | 4.96 | 4.61 | 4.64 | 4.24 |
| Solution-pH 7-8 | 7.31 | 4.98 | 4.71 | 4.74 | 4.28 |
| In situ gel-pH 7-8 | 7.61 | 5.03 | 4.67 | 4.57 | 4.2 |
| Solution-pH 8-9 | 8.47 | 5.05 | 4.76 | 4.89 | 4.42 |
| In situ gel-pH 8-9 | 8.58 | 5.14 | 4.77 | 5.07 | 4.52 |

TABLE 15

The stability of povidone iodine solution (Available iodine) and povidone iodine in situ gel formulation in different pH range

| Example 12 | Available Iodine (%) | | | | | | | | Remaining |
|---|---|---|---|---|---|---|---|---|---|
| | 0 day | | | Average | 5 day | | | Average | |
| NS-(2~4) | 10.62 | 10.62 | 10.62 | 10.62 | 10.23 | 10.23 | 10.23 | 10.23 | 96.33% |
| DGG-(2~4) | 10.63 | 10.63 | 11.09 | 10.78 | 10.68 | 10.68 | 10.68 | 10.68 | 99.04% |
| NS(4~5) | 11.1 | 11.1 | 10.63 | 10.94 | 10.68 | 10.68 | 10.24 | 10.53 | 96.25% |
| DGG(4~5) | 10.62 | 10.62 | 10.62 | 10.62 | 10.18 | 10.23 | 10.18 | 10.20 | 96.01% |
| NS(5~6) | 11.09 | 11.09 | 10.63 | 10.94 | 10.24 | 10.24 | 10.24 | 10.24 | 93.63% |
| DGG(5~6) | 10.16 | 10.62 | 10.62 | 10.47 | 10.22 | 10.22 | 9.33 | 9.92 | 94.81% |
| NS(6~7) | 10.63 | 10.63 | 10.17 | 10.48 | 9.35 | 9.79 | 9.35 | 9.50 | 90.65% |
| DGG(6~7) | 10.61 | 11.07 | 10.15 | 10.61 | 9.33 | 10.22 | 9.77 | 9.77 | 92.11% |
| NS(7~8) | 11.07 | 11.07 | 11.07 | 11.07 | 10.66 | 10.66 | 10.66 | 10.66 | 96.30% |
| DGG(7~8) | 11.09 | 10.63 | 10.63 | 10.78 | 10.23 | 10.23 | 10.23 | 10.23 | 94.87% |
| NS(8~9) | 10.61 | 10.15 | 10.15 | 10.30 | 9.77 | 10.21 | 10.21 | 10.06 | 97.67% |
| DGG(8~9) | 10.63 | 10.63 | 10.63 | 10.63 | 10.23 | 10.23 | 10.23 | 10.23 | 96.24% |

| Example 12 | Available Iodine (%) | | | Remaining |
|---|---|---|---|---|
| | 10 day | | Average | |
| NS-(2~4) | 10.29 | 10.29 | 10.29 | 10.29 | 96.89% |
| DGG-(2~4) | 10.75 | 10.3 | 10.75 | 10.60 | 98.30% |
| NS(4~5) | 10.3 | 10.75 | 10.3 | 10.45 | 95.49% |
| DGG(4~5) | 9.85 | 10.3 | 10.3 | 10.15 | 95.57% |
| NS(5~6) | 10.3 | 10.3 | 10.3 | 10.30 | 94.18% |
| DGG(5~6) | 9.84 | 9.84 | 9.84 | 9.84 | 94.01% |
| NS(6~7) | 9.85 | 9.85 | 9.41 | 9.70 | 92.62% |
| DGG(6~7) | 9.84 | 9.84 | 9.84 | 9.84 | 92.74% |
| NS(7~8) | 10.73 | 10.73 | 10.73 | 10.73 | 96.93% |
| DGG(7~8) | 10.3 | 10.3 | 9.85 | 10.15 | 94.13% |
| NS(8~9) | 9.83 | 10.28 | 10.28 | 10.13 | 98.32% |
| DGG(8~9) | 10.3 | 9.85 | 9.85 | 10.00 | 94.07% |

TABLE 15-continued

The stability of povidone iodine solution (Available iodine) and
povidone iodine in situ gel formulation in different pH range

| Example12 | Available Iodine | | | | | | | | | |
|---|---|---|---|---|---|---|---|---|---|---|
| | 20 day | | | Average | Remaining | 30 day | | | Average | Remaining |
| NS-(2~4) | 10.29 | 10.65 | 10.21 | 10.38 | 97.77% | 9.32 | 9.3 | 9.3 | 9.31 | 87.63% |
| DGG-(2~4) | 9.33 | 9.77 | 9.77 | 9.62 | 89.24% | 8.87 | 9.31 | 9.31 | 9.16 | 84.98% |
| NS(4~5) | 9.77 | 9.77 | 9.77 | 9.77 | 89.28% | 9.76 | 9.31 | 10.2 | 9.76 | 89.16% |
| DGG(4~5) | 9.77 | 9.77 | 9.77 | 9.77 | 92.00% | 9.75 | 9.31 | 9.75 | 9.60 | 90.43% |
| NS(5~6) | 9.77 | 9.77 | 9.77 | 9.77 | 89.33% | 9.76 | 9.76 | 9.76 | 9.76 | 89.24% |
| DGG(5~6) | 9.76 | 9.76 | 9.76 | 9.76 | 93.25% | 9.74 | 8.86 | 9.3 | 9.30 | 88.85% |
| NS(6~7) | 8.88 | 9.33 | 9.77 | 9.33 | 89.02% | 8.87 | 8.87 | 8.87 | 8.87 | 84.66% |
| DGG(6~7) | 9.31 | 8.87 | 9.31 | 9.16 | 86.37% | 9.29 | 8.85 | 8.85 | 9.00 | 84.79% |
| NS(7~8) | 9.75 | 9.75 | 9.75 | 9.75 | 88.08% | 9.73 | 9.29 | 9.29 | 9.44 | 85.25% |
| DGG(7~8) | 9.33 | 9.33 | 8.88 | 9.18 | 85.13% | 9.31 | 8.87 | 8.87 | 9.02 | 83.62% |
| NS(8~9) | 9.31 | 9.31 | 9.75 | 9.46 | 91.78% | 9.29 | 9.29 | 9.29 | 9.29 | 90.16% |
| DGG(8~9) | 9.33 | 9.33 | 9.33 | 9.33 | 87.77% | 9.75 | 9.31 | 8.87 | 9.31 | 87.58% |

Figure 13:
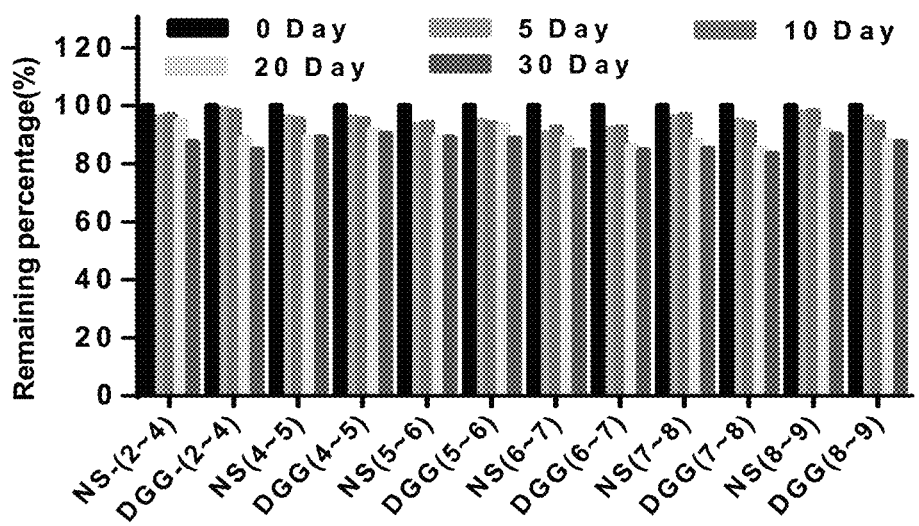
FIG. 13 shows the stability of a PVP-I solution and an ophthalmic formulation of this invention containing PVP-I at 25° C., with different ranges of pH values.

As the result shown in Table 15 and FIG. 13, after storage at 25° C. for 30 days, the stability of PVP-I solution and the formulations of this invention containing PVP-I with pH range of 4-5 and 5-6, was slightly better than that with other pH conditions. Moreover, it is observed that the stability of the formulations of this invention containing PVP-I was consistently better than that of PVP-I solution.

Example 13

Evaluation of the stability of low-concentration povidone-iodine eye drops. The stability of low-concentration PVP-I solutions in two different formulations was investigated. Formulations of this invention containing PVP-I and PVP-I solution were prepared according to Table 16. Their pH was adjusted to 5.0-5.5 with NaOH, and the stability was evaluated at 25° C. The concentration of povidone-iodine was determined by sodium thiosulfate titration (n=3).

TABLE 16

Formulations of two formulations containing low-concentration PVP-I

| Ingredient | 0.3% in situ gel Formulation (0.3% F.) | 0.3% solution Control (0.3% C.) |
|---|---|---|
| DGG | 0.30 g | — |
| PVP-I | 0.30 g | 0.30 g |
| NaCl | 0.30 g | 0.35 g |
| Dexamethasone | — | 0.10 g |
| EDTA | — | 0.01 g |
| Tyloxapol | — | 0.05 g |
| Anhydrous sodium sulfate | — | 1.20 g |
| Hydroxylethyl cellulose | — | 0.25 g |
| Distilled water | 100 mL | 100 mL |
| pH | 5.5 | 5.5 |

TABLE 17

Stability of two low-concentration of PVP-I solutions (Available Iodine)

Available Iodine (%)

| | 0 day | | | Avg | 7 day | | | Avg | Remaining % |
|---|---|---|---|---|---|---|---|---|---|
| F 0.3% | 11.00 | 11.46 | 10.95 | 11.14 | 11.01 | 10.80 | 10.86 | 10.89 | 98% |
| C 0.3% | 10.93 | 13.16 | 12.79 | 12.29 | 11.09 | 10.72 | 10.84 | 10.88 | 89% |

| | 14 day | | | Avg | Remaining % | 21 day | | | Avg | Remaining % |
|---|---|---|---|---|---|---|---|---|---|---|
| F 0.3% | 10.64 | 10.72 | 8.82 | 10.06 | 90% | 10.95 | 8.67 | 10.67 | 10.10 | 91% |
| C 0.3% | 12.46 | 10.73 | 8.78 | 10.66 | 87% | 12.20 | 10.46 | 10.43 | 11.03 | 90% |

Figure 14:
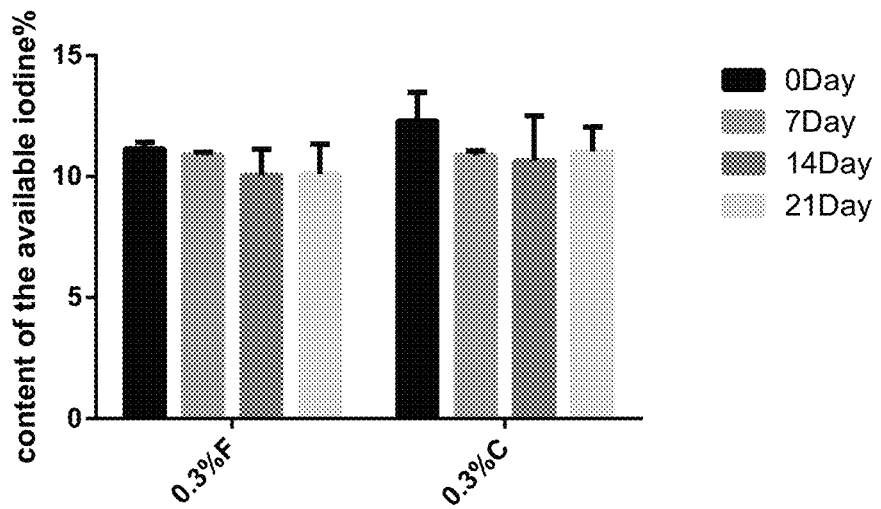
FIG. 14 shows the stability of a low-concentration PVP-I solution and an ophthalmic formulation of this invention containing PVP-I at 25° C.

As the results shown in Table 17 and FIG. 14, the stability of Formulations of this invention containing PVP-I was better than that of PVP-I solutions after storage at 25° C. for 21 days.

Example 14 In Vitro Dissolution Experiment

Formulations of this invention containing PVP-I was prepared according to the formulations set out in Table 18. 2 g sample was measured precisely (about 2 ml) and then added into a vial of 22 mm outer diameter, followed by addition of 350 μL simulated tear fluid (STF) and mixing quickly. The mixture was covered with a stopper and weighed precisely and recorded. Placed samples into an air shaker (34.5° C., 120 r/min), balanced for 10 min, and added simulated tear fluid (pre-heated to 34.5° C., 2 ml) along the side-wall slowly, took out all of the release medium at a different point in time, weighed quickly and recorded. 10 minute rebalance was needed after each shaking; took out the release medium before adding fresh STF (pre-heated to 34.5° C.); repeated this process until gel was dissolved completely. Draw gel dissolution time curve (n=3) by plotting the total amount of gel dissolution vs time.

TABLE 18

Formulations of this invention containing PVP-I

| | DGG (w/w) | PVP-I (w/w) | NaCl (w/w) | pH |
|---|---|---|---|---|
| Formulation (G) | 0.2%<br>0.3%<br>0.4% | 0.6% | 0.3% | 5.0~5.5 |

Figure 15:
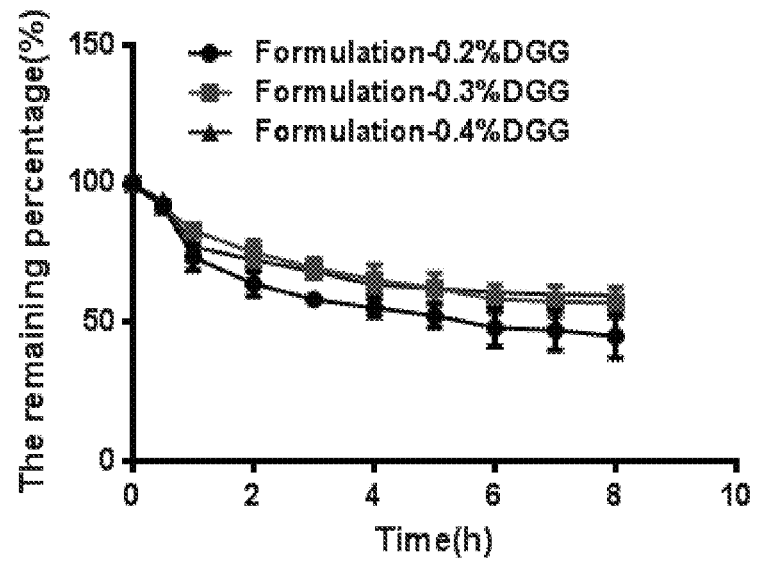
FIG. 15 shows the dissolution curve of ophthalmic formulations of this invention containing PVP-I and DGG at different concentrations.
Figure 16:
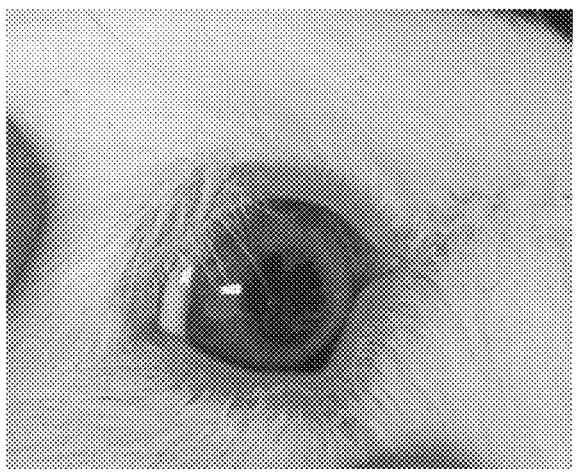
FIG. 16 shows in situ gel formulation in rabbit eyes (which can be observed with naked eyes) after Formulation-0.3% G was instilled into the rabbit eyes.

As the results shown in Table 18 and FIG. 15, formulations of this invention containing PVP-I and 0.2% (w/w) showed a good ability to retard tear erosion. There was still about 40% of matrix that was not dissolved after 8 hours of simulated tear fluid-flushing. With the increase of concentration of deacetylated gellan gum, the dissolution of the formulations of this invention containing PVP-I became even slower, which effectively prolonged the residence time of PVP-I in the eye.

Example 15 Evaluate Irritation of Formulations of this Invention Containing PVP-I Evaluate eye damage severity according to eye irritation test (Draize test); criteria: 10 adult New Zealand white rabbits was taken (body weight 2.0-2.5 kg) and administered with 30 μL drug into intraocular capsule. Closed the rabbit eyes for 5-10 seconds passively after administration. According to scoring criteria, added all scores of the stimulus response of cornea, iris, and conjunctiva of each animal; the total score was a test animal eye irritation response. The final score of formulations of this invention containing PVP-I against ocular irritation was the total score of every animal stimulus response divided by the number of animals. The degree of ocular irritation was determined by the criteria.

The test results showed that the rabbit's eyes were natural and comfortable after administering formulations of this invention containing PVP-I; it had small amount of secretions, making eyelids and eyelashes moist or sticky; however, it was regarded as minimum irritation according to eye injury severity scoring criteria (Draize test).

Rabbit eye blinking test: Adult New Zealand rabbit (body weight ranging from 2.0 to 2.5 kg) werr administrated with 304 drug into left and right eye conjunctival sac respectively, closed rabbit eye for 5-10 seconds passively after administration. Recorded the numbers of blinks within 90 seconds after administration (n=10). The test groups were as follows: 1) normal saline group (NS); 2) 0.4% DGG blank matrix group (Control); 3) povidone iodine eye drop solution group (PVP-I+NS); 4) povidone iodine in situ gel eye drop formulation with DGG concentration of 0.2%, 0.3%, 0.4% (PVP-I in situ gel).

TABLE 19

The formulation of povidone iodine compositions

| No. | NS | 0.3% Gellan gum blank | PVP-I Eye drop | Formulation--0.2% G | Formulation--0.3% G | Formulation--0.4% G |
|---|---|---|---|---|---|---|
| 1 | 2 | 2 | 10 | 11 | 7 | 5 |
| 2 | 3 | 3 | 11 | 11 | 7 | 5 |
| 3 | 2 | 3 | 5 | 4 | 8 | 3 |
| 4 | 2 | 4 | 8 | 4 | 8 | 4 |
| 5 | 2 | 4 | 5 | 5 | 5 | 6 |
| 6 | 2 | 3 | 5 | 5 | 7 | 6 |
| 7 | 2 | 3 | 9 | 5 | 5 | 4 |
| 8 | 3 | 3 | 10 | 6 | 6 | 4 |
| 9 | 2 | 1 | 6 | 4 | 3 | 8 |
| 10 | 2 | 2 | 7 | 4 | 3 | 8 |
| Average | 2.2 | 2.8 | 7.6 | 5.9 | 5.9 | 5.3 |
| SD | 0.4216 | 0.9189 | 2.3190 | 2.7669 | 1.8529 | 1.7029 |
| p | | | | 0.077 | 0.043 | 0.010 |

Figure 17:
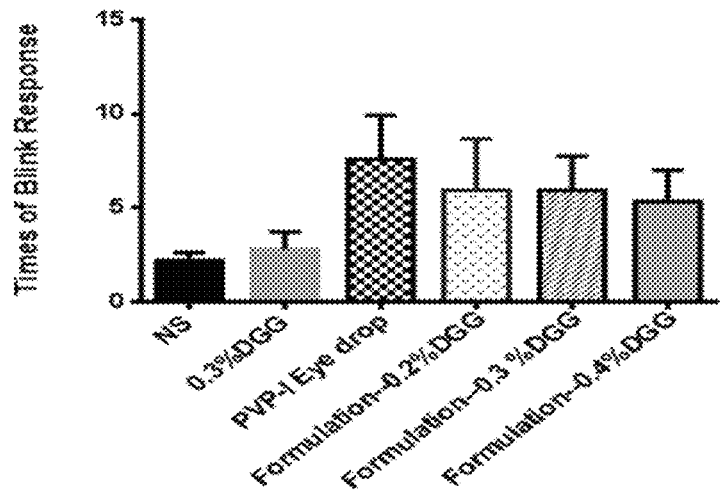
FIG. 17 shows result of irritation evaluation of a PVP-I solution and an ophthalmic formulation of this invention containing PVP-I in rabbit eyes (n=10).

As the results shown in Table 19 and FIG. 17, the gel matrix used in this formulation had no irritation. The rabbit eyes were natural and blinked normally at 2-3 times within 90 seconds after administration of NS or 0.3% DGG. Povidone iodine eye drops (solution) had the most irritation to rabbit eye, and the rabbit eye blinked frequently after administration with average 8 times within 90 seconds. More than half of rabbits' eyes were in semi-closed state due to stimulating, secretions increased. However, it was surprisingly found that the rabbit eye blinked 4-5.75 time within 90 seconds and there was no swelling, blood congestion observed in rabbit eye for the PVP-I in situ gel formulation testing groups. In the tested groups with formulations of this invention (0.3% G and 0.4% G), statistically significant less irritation was shown than the PVP-I solution test group with p=0.043 and 0.01, respectively. Both p<0.05. It indicated that the main irritation of PVP-I formulation came from PVP-I itself. The test results showed that the formulations of this invention containing PVP-I exhibited much less irritation than traditional PVP-I eye drop solution formulations.

Example 16 In Vitro Release Test

Took 2 mL formulations of this invention containing PVP-I or 2 mL PVP-I normal saline solution, placed in a 14 KDa dialysis bag, added into 50 mL simulated tear fluid with pre-warmed to 34.5° C., shook samples via air shaker at 120 rpm, took out the release medium STF every 30 minutes, and added fresh release medium (pre-warmed to 34.5° C.) quickly. Determined available iodine concentration by sodium thiosulfate titration (n=3), and calculated its accumulative release amount.

Figure 18:
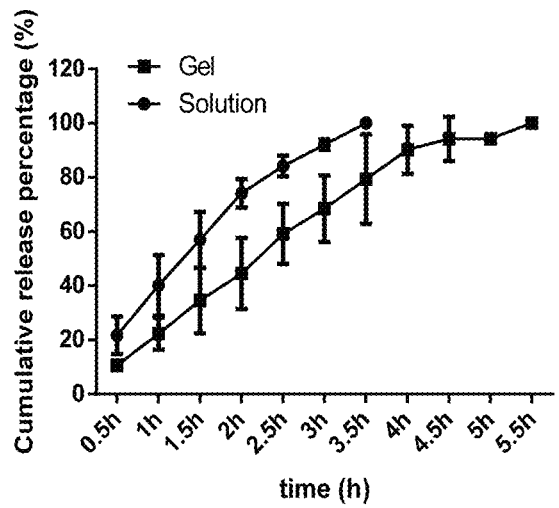
FIG. 18 shows an in vitro cumulative release curve of a PVP-I solution and an ophthalmic formulation of this invention containing PVP-I in rabbit eyes (n=3).

As the results shown in FIG. 18, formulations of this invention containing PVP-I had a significantly sustained-release character comparing with conventional povidone iodine eye drop solutions, and extended PVP-I release steadily for about 5 hours.

Example 17 Evaluate Ophthalmic Retention Ability

Placed 1 ml normal saline and formulations of this invention containing PVP-I in brown EP tube, added 0.5% fluorescein sodium respectively. Chose a healthy New Zealand rabbit, and made its head fixed. Dropped 50 μL fluorescent labeled PVP-I normal saline solution into its left eye and made it close passively for 10 s. Observed fluorescence condition of left eyes at 0 min, 2 min, 4 min, 6 min, 8 min and 10 min via slit lamp; dropped 50 μl formulations of this invention containing PVP-I into its right eye and made it close passively for 10 seconds. Observed fluorescence conditions of the right eyes at 0 min, 2 min, 5 min, 10 min, 20 min 30 min, 40 min, 50 min and 60 min with slit lamp.

Figure 19:
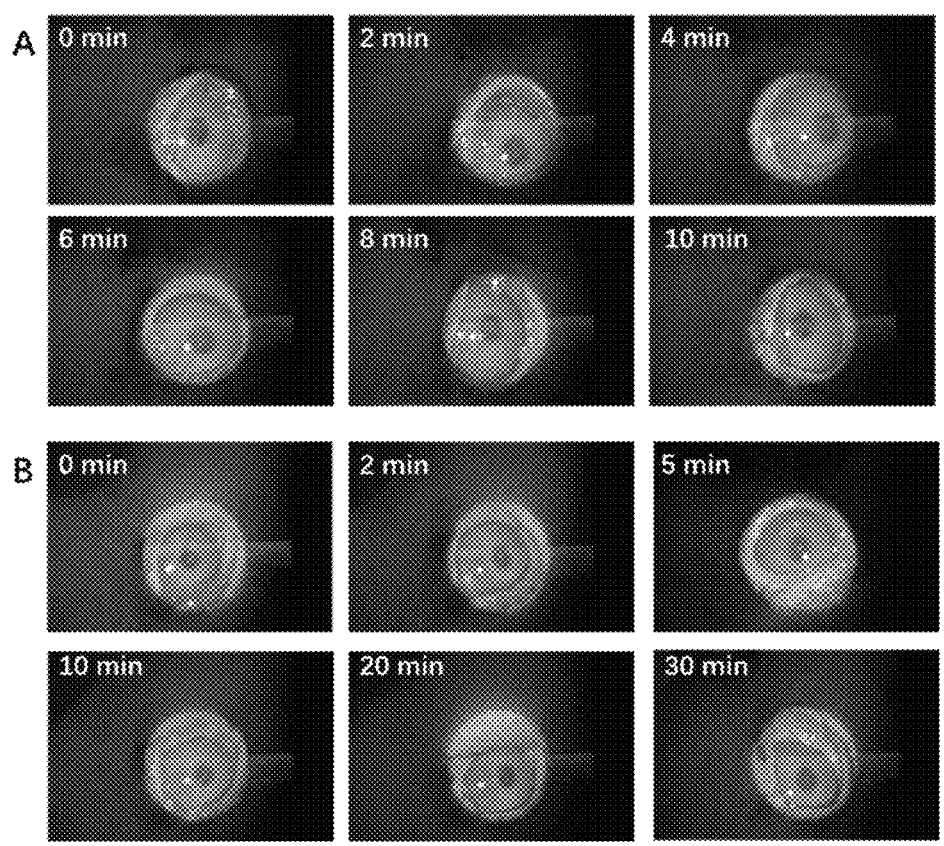
FIG. 19 shows the fluorescence photographs of a PVP-I solution and the retention of an ophthalmic formulation of this invention containing PVP-I in rabbit eyes.

As the results shown in FIG. 19, conventional PVP-I eye drop solutions was quickly eliminated after administration, and was retained for only 4 min in rabbit conjunctival sac. By contrast, the elimination rate formulations of this invention containing PVP-I was slowed down significantly after administration, and it could be retained in rabbit conjunctival sac for more than 20 min. The results showed that formulations of this invention containing PVP-I extended povidone iodine efficacious time in eyes significantly longer and made the formulation long-acting.

Example 18 Chlorhexidine extended release in situ ophthalmic formulations

In another embodiment, the in situ gel forming materials are not limited to polysaccharides described in the examples. The in-situ gel forming chlorhexidine digluconate compositions can be formulated with one or more ion-activated in-situ gel forming materials. The polymeric in-situ gel forming agents may include but not limited to dextrans, polyethylene glycols, polyvinylpyrolidone, polysaccharide gels, Gelrite®, alginate, sodium alginate, sodium hyaluronate, hyaluronic acid, cellulosic polymers like hydroxypropyl methylcellulose, and carboxy-containing polymers such as polymers or copolymers of acrylic acid, as well as other polymeric demulcents. One or more in-situ gel formation agents can be selected in the compositions. Preferred polymeric in-situ gel forming agents can be Deacetylated gellan gum (Gelrite®).

Example 19. Formulations of this Invention Containing PVP-I for Skin and Vaginal Disinfection Formulations of this invention containing PVP-I can be studied for their extended release of PVP-I on infected skin and in the infected vagina in the same manner as described above and are expected to have much longer lasting effect than the PVP-I solutions without the gelling effect.

The above-mentioned compositions can be further combined with an artificial tear-based lubricant to improve the comfort of the povidone-iodine solution. The povidone-iodine is prepared in the abovementioned sustained release formulation and combined with artificial-tear based lubricants that may include but are not limited to Propylene glycol, glycerin, propylene glycol, blended polyvinyl alcohols, Polyvinyl Alcohol, Polyethylene Glycol 400, light mineral oil, hydroxypropyl methylcellulose, hypromellose, Carbopol 980, White petrolatum, Soy lecithin, sodium carboxyl methylcellulose, hydroxypropyl methylcellulose, hypromellose.

In a preferred embodiment, the povidone-iodine (PVP-I) is between 0.1% and 2.5%, between 0.3 and 2%, between 0.3 and 1.5%, or between 0.3% and 1.0%.

The ophthalmic compositions may further comprise (1) a topical anesthetic which relieves pain (2) a penetration enhancer which enhances the penetration of povidone-iodine into the tissues of the eye, for example, Azone (laurocapram) a glucan sulfate such as dextran sulfate, cyclodextrin sulfate, and β-1,3-glucan sulfate (3) an antimicrobial preservative, which, for example, may be at a concentration of about 0.001% to 1.0% by weight; (4) a co-solvent or a nonionic surface agent—surfactant, which, for example, may be about 0.01% to 2% by weight; (5) viscosity increasing agent, which, for example, may be about 0.01% to 2% by weight; (6) a cooling agent such as menthol, menthol derivatives including methane glycerin acetyl and methyl esters, carboxamides, methane glycerol ketals, alkylsubstituted ureas, sulfonamides, terpene analogs, furanones, and phosphine oxides; or camphor, and borneol, which can provide coolness sensation on the eye; and (7) other medicaments such as anti-inflammatories, steroids, and NSAIDs.

The compositions are useful in the treatment of infections of the conjunctiva and cornea. In another embodiment, the invention is directed to a method for treating and/or prophylaxis of an eye disorder or a microorganism infection of at least one tissue of the eye comprising the step of administering one of more doses of an ophthalmic composition, discussed above, to the eye. The eye disorder may be, for example, a microorganism infection of at least one tissue of the eye, conjunctivitis, corneal abrasion, ulcerative infectious keratitis, epithelial keratitis, stromal keratitis and herpesvirus-related keratitis. The microorganism may be bacteria (e.g., mycobacteria), virus, fungi, or amoebae.

One embodiment of the invention is directed to an ophthalmic composition suitable for topical administration to an eye, effective for treatment and/or prophylaxis of a microorganism infection or a disorder of at least one tissue of the eye. Prophylaxis may be, for example, prophylaxis from infection following surgery, prophylaxis from infection after birth for the newborn, or prophylaxis from accidental contact with contaminating material. Accidental contact with contaminating material may occur, for example, during surgery or during food processing.

In the method, the treatment may comprise administering a formulation of the invention where the weight of the PVP-I is between 0.001 mg to 5 mg per dose. Further, the dose volume may be between 10 microliters to 200 microliters or between 50 microliters to 80 microliters; about one drop per eye. Administration may be between 1 to 24 times a day, between 2 to 4 times a day or between 2 to 24 times a day.

Suitable topical anesthetics for the compositions and methods of the invention include, at least, proparacaine, lidocaine, tetracaine or a derivative or combination thereof.

In any of the compositions of this disclosure for topical administration, such as topical administration to the eye, the mixtures are preferably formulated as 0.01 to 2.0 percent by weight solutions in water at a pH of 5.0 to 8.0. This pH range may be achieved by the addition of acids/bases or buffers to the solution. While the precise regimen is left to the discretion of the clinician, it is recommended that the resulting solution be topically applied by placing one drop in each eye 1 to 24 times daily. For example, the solution may be applied 1, 2, 4, 6, 8, 12, 18 or 24 times a day.

Antimicrobial Preservative

As an optional ingredient, suitable antimicrobial preservatives may be added to prevent multi-dose package contamination, though povidone-iodine will serve as self-preservative. Such agents may include benzalkonium chloride, thimerosal, chlorobutanol, methyl paraben, propyl paraben, phenylethyl alcohol, EDTA, sorbic acid, Onamer M, other agents known to those skilled in the art, or a combination thereof. Typically such preservatives are employed at a level of from 0.001% to 1.0% by weight.

Co-Solvents/Surfactants

The compositions of the invention may contain an optional co-solvent. The solubility of the components of the present compositions may be enhanced by a surfactant or other appropriate co-solvent in the composition. Such co-solvents/surfactants include polysorbate 20, 60, and 80, polyoxyethylene/polyoxypropylene surfactants (e.g. Pluronic F-68, F-84 and P-103), cyclodextrin, tyloxapol, other agents known to those skilled in the art, or a combination thereof. Typically such co-solvents are employed at a level of from 0.01% to 2% by weight.

Viscosity Agents

The compositions of the invention may contain an optional viscosity agent—that is, an agent that can increase viscosity. Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity builder agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof. Such agents are typically employed at a level of from 0.01% to 2% by weight.

The invention has been described herein by reference to certain preferred embodiments. However, as obvious variations thereof will become apparent to those skilled in the art, the invention is not to be considered as limited thereto. All patents, patent applications, and references cited anywhere is hereby incorporated by reference in their entirety.

What is claimed is:

1. An aqueous formulation comprising povidone-iodine as an antiseptic agent, a biocompatible polysaccharide, an osmotic pressure regulator, a pH regulator, and water, wherein the antiseptic agent is contained in the formulation at 0.1% to 5.0% weight/weight or weight/volume, the biocompatible polysaccharide comprises deacetylated gellan gum which is contained in the formulation at the concentration ranging from 0.1% to 1.0% weight/weight, and a gel containing the antiseptic agent is formed in situ at physiological temperature with instant viscosity increase upon instillation of the formulation onto a body cavity of a subject.

2. The aqueous formulation of claim 1, wherein the antiseptic agent is contained in the formulation at 0.1% to 1.0% weight/weight or weight/volume.

3. The aqueous formulation of claim 2, wherein the antiseptic agent is contained in the formulation at 0.3% to 1.0% weight/weight or weight/volume.

4. The aqueous formulation of claim 1, wherein the polysaccharide is contained in the formation at 0.1% to 0.5% weight/weight.

5. The aqueous formulation of claim 4, wherein the polysaccharide is contained in the formation at 0.3% to 0.4% weight/weight.

6. The aqueous formulation of claim 1, wherein the polysaccharide further comprises xanthan, sodium alginate, carrageenan, or any mixture thereof.

7. The aqueous formulation of claim 1, wherein the osmotic pressure regulator comprises sodium chloride, glycerol, polyethylene glycol 400, mannitol, or boric acid.

8. The aqueous formulation of claim 1, wherein the osmotic pressure regulator comprises sodium chloride and mannitol.

9. The aqueous formulation of claim 1, wherein the osmotic pressure regulator is contained in the formulation at 0.1 to 0.5% weight/volume.

10. The aqueous formulation of claim 1, wherein the osmotic pressure regulator is contained in the formulation at 0.2 to 0.4% weight/volume.

11. The aqueous formulation of claim 1, wherein the pH regulator comprises sodium hydroxide, tris(hydroxymethyl) aminomethane, tris(hydroxymethyl)aminomethane HCl, phosphoric acid, or any mixture thereof.

12. The aqueous formulation of claim 11, wherein the pH regulator comprises tris(hydroxymethyl)aminomethane.

13. The aqueous formulation of claim 1, wherein the formulation has a pH value in the range of 4.0 to 7.0.

14. The aqueous formulation of claim 12, wherein the formulation has a pH value in the range of 4.0 to 6.0.

15. The aqueous formulation of claim 1, wherein the body cavity of a subject is the eye, nose, or vagina, has infection, and is in need of a treatment.

16. The aqueous formulation of claim 15, wherein the infection is conjunctivitis, corneal abrasion, ulcerative infectious keratitis, epithelial keratitis, stromal keratitis, herpes virus-related keratitis, chronic rhinosinusitis, acute rhinosinusitis, or vaginitis.

17. A method for treating an ocular infectious disease, comprising administering a therapeutically effective amount of an aqueous ophthalmic formulation of claim 1 to a person in need thereof, wherein the ocular infectious disease is conjunctivitis, corneal abrasion, ulcerative infectious keratitis, epithelial keratitis, stromal keratitis, or herpes virus-related keratitis.

* * * * *